United States Patent [19]
Spillane et al.

[11] Patent Number: 5,385,036
[45] Date of Patent: Jan. 31, 1995

[54] WARP KNITTED TEXTILE SPACER FABRIC, METHOD OF PRODUCING SAME, AND PRODUCTS PRODUCED THEREFROM

[75] Inventors: Robert T. Spillane, Greensboro, N.C.; Mike S. Kowalski, Derbyshire, United Kingdom

[73] Assignee: Guilford Mills, Inc., Greensboro, N.C.

[21] Appl. No.: 67,208

[22] Filed: May 24, 1993

[51] Int. Cl.[6] .................. D04B 1/00; A41D 13/08
[52] U.S. Cl. .................................. 66/87; 2/16; 602/63; 66/196
[58] Field of Search .............. 66/87, 88, 192, 194, 66/195, 196, 202; 2/16, 22; 602/63

[56] References Cited

U.S. PATENT DOCUMENTS

| | | | |
|---|---|---|---|
| 3,685,319 | 8/1972 | Jackson | 66/87 R |
| 3,864,944 | 2/1975 | Jackson | 66/196 X |
| 3,866,443 | 2/1975 | Hunneke et al. | 66/194 |
| 3,899,900 | 8/1975 | Jackson | 66/87 |
| 3,945,052 | 3/1976 | Liebig | 3/1 |
| 4,302,953 | 12/1981 | Wilkens | 66/87 |
| 4,315,419 | 2/1982 | Kernbichler et al. | 66/87 |
| 4,430,811 | 2/1984 | Okada | 36/45 |
| 4,601,940 | 7/1986 | Fischer | 428/178 |
| 4,785,558 | 11/1988 | Shiomura | 36/114 |
| 4,787,219 | 11/1988 | Sato et al. | 66/190 |
| 4,813,161 | 3/1989 | Lesley | 36/44 |
| 4,832,010 | 5/1989 | Lerman | 602/63 |
| 4,914,836 | 4/1990 | Horovitz | 36/28 |
| 5,077,837 | 1/1992 | Meistrell | 2/16 |

FOREIGN PATENT DOCUMENTS

| | | | |
|---|---|---|---|
| 1201898 | 3/1986 | Canada. | |
| 3139402 | 4/1983 | Germany | 66/196 |
| 0059336 | 12/1985 | Japan | 66/196 |
| 2229247 | 9/1990 | Japan | 66/196 |
| 1216266 | 3/1986 | U.S.S.R. | 66/196 |
| 1254072 | 8/1986 | U.S.S.R. | 66/196 |

Primary Examiner—Clifford D. Crowder
Assistant Examiner—John J. Calvert
Attorney, Agent, or Firm—Shefte, Pinckney & Sawyer

[57] ABSTRACT

A warp knitted textile spacer fabric, a process for producing same, and articles utilizing same are disclosed. The spacer fabric is of an at least six-bar Raschel construction produced on a double needle bar Raschel knitting machine by knitting front and back stretchable fabric substructures of respective sets of ground and elastic yarns interknitted with one another in a stretchable resilient stitch construction while simultaneously knitting at least two sets of monofilament pile yarns in a pile substructure integrated with and extending between the fabric substructures to form pile segments extending transversely between the fabric substructures in differing angular orientations to the widthwise and lengthwise dimensions of the fabric, producing a pyramidal truss-like system of pile segments which maintain the fabric substructures in spaced parallel relation yet are resiliently compressible and resist relative shear movements of the fabric substructures. The present spacer fabrics effectively simulate the stretchability, compressibility and resiliency of conventional plastic foam materials such as neoprene while providing enhanced air and moisture permeability. Under the present process, the spacer fabric may be heat set in a predetermined stretched condition following knitting to selectively engineer the fabric's physical and aesthetic characteristics. An athletic shoe and a knee brace are disclosed as representative products utilizing these spacer fabrics.

68 Claims, 8 Drawing Sheets

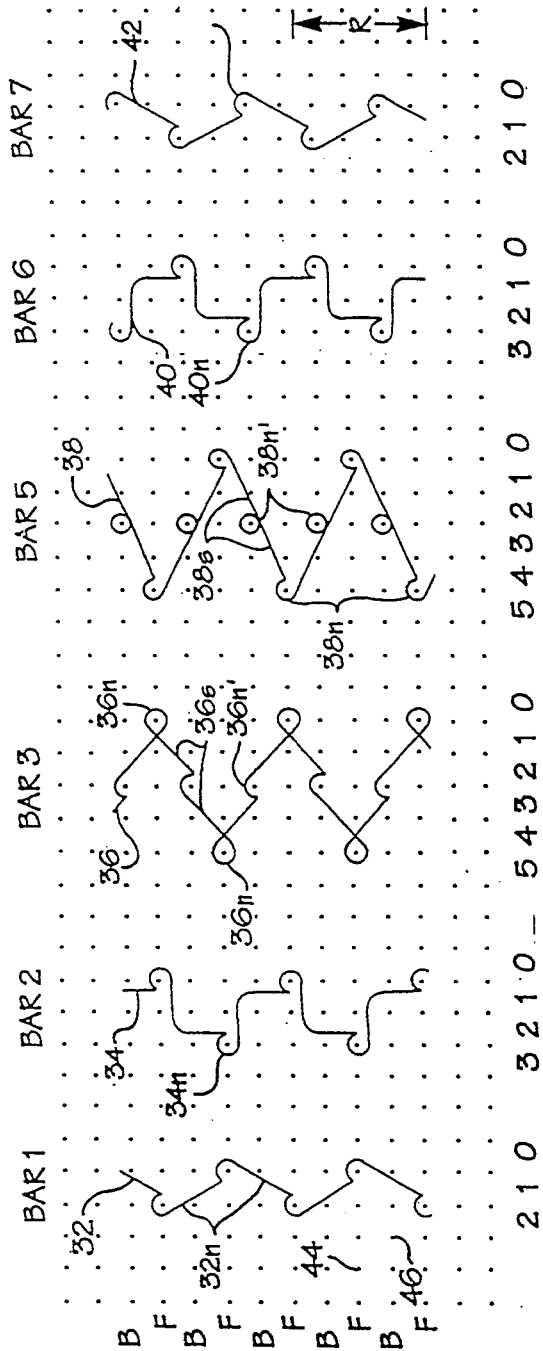
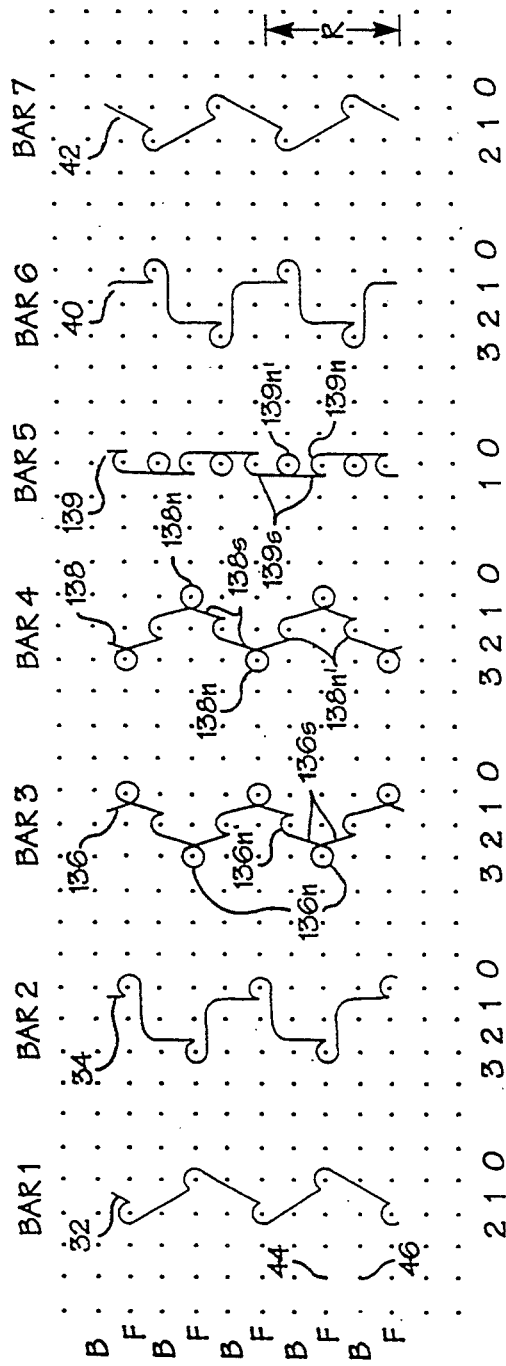
Fig. 3
Fig. 7

WARP KNITTED TEXTILE SPACER FABRIC, METHOD OF PRODUCING SAME, AND PRODUCTS PRODUCED THEREFROM

BACKGROUND OF THE INVENTION

The present invention relates generally to textile fabrics and fabric producing methods and, more particularly, to warp knitted textile fabrics of the type commonly referred to as spacer or double plush Raschel fabrics produced on a double needle bar Raschel warp knitting machine, to products produced from such fabrics, and to warp knitting methods for producing such fabrics.

Double needle bar Raschel warp knitting machines are basically equipped with two independently operated needle bars fed with multiple warps of yarn from a plurality of respective warp beams through a corresponding plurality of yarn guide bars. One common application of such knitting machines is to produce a so-called spacer or double plush pile fabric having two separate spaced-apart ground fabric structures integrated by one or more traversing yarns extending between and interknitted with the two ground structures. Spacer fabrics of this type are typically produced from five or more sets of warp yarns separately wound on individual warp beams and fed to the two needle bars through a corresponding set of yarn guide bars, normally with at least two sets of warp yarns fed through two corresponding guide bars exclusively to one of the needle bars to fabricate one ground structure, at least two other sets of warp yarns fed through other corresponding guide bars exclusively to the other needle bar to fabricate the other ground structure, and the remaining sets of warp yarns fed through one or more of the remaining available guide bars alternately to the two needle bars to extend between and interknit with the two ground structures and thereby to integrate and maintain the ground structures in spaced-apart essentially parallel relation.

Traditionally, double needle bar Raschel spacer fabrics of this type have been utilized as a means of producing two warp-knitted pile fabrics at once, the two ground structures of the spacer fabric being separated subsequent to knitting by a cutting operation wherein a cutting blade severs the traversing yarns intermediate the two ground structures leaving each ground structure with a plush pile surface produced by the outwardly extending portions of the severed yarns. More recently, however, attention has been directed to applications and uses of double needle bar Raschel spacer fabrics which are left intact as knitted without undergoing any cutting operation. Because the traversing pile yarns in such fabrics lend a three-dimensional quality to the fabrics and provide some degree of compressibility and resiliency across the thickness of the fabric, it has been proposed that such fabrics could be utilized as an acceptable substitute for conventional fabric-laminated foam materials such as neoprene and polyurethane.

Such applications of spacer fabrics offer several potentially significant advantages. First, since many textile fiber and filamentary materials are recyclable, the use of spacer fabrics as a cushioning material overcomes the inability of foams to be recycled and the attendant problems associated with disposal of such materials. Also, spacer fabrics offer substantially enhanced air and moisture permeability over foams, which makes such fabrics more desirable than foam materials for use in shoes, foundation garments, other garments, medical supports and wraps, athletic wraps and braces, etc., worn on the body. Additionally, spacer fabrics would eliminate the common necessity of laminating a fabric material to one or both surfaces of a foam material and thereby have the potential for improved production efficiency and lower cost in comparison to fabric-backed foam materials.

On the other hand, spacer fabrics present some difficulty in replicating certain of the physical characteristics of foam materials such as compressibility, resiliency, modulus and power. While spacer fabrics have a certain degree of inherent compressibility and resiliency, it has proven difficult in practice to engineer and design for any given conventional foam material a spacer fabric which is comparable both in physical characteristics of compressibility, resiliency, stretchability, modulus and power and in dimensional thickness as well, while also achieving a comparable hand and feel. Further, spacer fabrics characteristically have the tendency for the two opposing ground fabric structures to shift and move in parallel with respect to one another when opposing forces are applied to the opposite fabric surfaces in a direction parallel to the fabric's lengthwise or widthwise dimension, commonly referred to in the industry as shear.

SUMMARY OF THE INVENTION

It is accordingly an object of the present invention to provide a novel warp knitted textile spacer fabric of the double needle bar Raschel pile type having characteristics of stretchability, compressibility and resiliency simulative of conventional resilient foam materials while at the same time providing characteristics of air and moisture permeability substantially enhanced over such conventional foam materials. It is a further object of the present invention to provide a novel method of producing such spacer fabrics and to provide examples of products which can make advantageous use of such spacer fabrics.

The foregoing objects are achieved by the spacer fabric and method of the present invention. Basically, the present spacer fabric comprises front and back stretchable fabric substructures and a pile substructure integrated with and extending between the front and back fabric substructures for maintaining them in spaced parallel relation while being resiliently yieldable for compressibility of the front and back fabric substructures together and subsequent recovery thereof to their spaced parallel relation. Briefly summarized, the spacer fabric is warp knitted according to the present method on a double needle bar Raschel-type warp knitting machine to be of an at least six-bar warp knitted Raschel construction wherein each fabric substructure comprises at least a set of ground yarns, e.g., texturized polyester, and a set of stretchable yarns, preferably elastic yarns such as Lycra brand yarns produced by E. I. DuPont de Nemours and Company, of Wilmington, Del., which are interknitted with one another in a stretchable resilient stitch construction. The pile substructure comprises at least two sets of monofilament pile yarns interknitted with each fabric substructure in a stitch construction forming pile segments which extend transversely between the fabric substructures in differing angular orientations relative to the widthwise and lengthwise dimensions of the spacer fabric for permitting resilient compressibility of the fabric substructures while resisting relative shear movement thereof in directions parallel thereto.

The use of monofilament pile yarns enhances the desirable characteristics of compressibility and resiliency in the spacer fabric, while the use of elastic or other stretchable yarns as one of the constituent yarns of each fabric substructure provides a stretchable character to the fabric. Preferably, the monofilament yarns are of relatively fine denier, e.g., in the range of about 40 denier and less and most preferably about 30 denier or less, so as to minimize any effect the monofilament pile yarns may have on the surface texture, hand and feel of the spacer fabric. It is known that spacer fabrics experience a relatively significant loss in width from the width of the fabric while constrained on the warp knitting machine to the relaxed width of the fabric after withdrawal from the machine. Accordingly, it is contemplated to be desirable to heat-set the spacer fabric under a predetermined partially stretched condition as a finishing step subsequent to knitting, which provides the two-fold advantage of enabling the physical characteristics of the fabric to be selectively engineered and also serves to effectively withdraw the monofilament pile yarns from the outward faces of the two fabric substructures to further improve the hand and feel of the spacer fabric.

More specifically, various six- and seven-bar constructions of the present spacer fabric are contemplated, six-bar constructions comprising two sets of monofilament pile yarns and seven-bar constructions comprising three sets of monofilament pile yarns. In most contemplated six- and seven-bar constructions, each pile yarn of two sets of pile yarns are preferably formed in successive needle loops which alternate every course between non-corresponding wales of the front and back fabric substructures, e.g., in alternating needle loops formed alternatingly in spaced wales of successive courses of one of the front and back fabric substructures and in intervening needle loops formed in a common wale of successive courses of the other fabric substructure. It is contemplated that the thickness of the spacer fabric can be selectively varied by varying the degree of spacing between the spaced wales of the alternating pile yarn needle loops, e.g., by varying the spacing by one, three, five or seven intervening wales of the respective fabric substructure. In seven-bar embodiments of the fabric, the third set of monofilament pile yarns is preferably interknitted with each fabric substructure in a chain stitch construction forming pile segments which extend transversely between the fabric substructures, e.g., in successive needle loops which alternate every course between corresponding wales of the front and back fabric substructures.

Most preferably, in the case of both six- and seven-bar embodiments of the spacer fabric, the pile segments of the pile yarns cooperate to act as a pyramidal system of triangularly related trusses for supporting and maintaining the front and back fabric substructures resiliently and compressibly in spaced parallel relation and for resisting relative shear movement thereof in response to forces exerted in directions generally parallel to the fabric substructures. In six-bar fabrics, each triangularly related pyramidal truss comprises four pile segments formed of a pair of pile segments of each of the two sets of pile yarns, with the four pile segments extending from four respective spaced-apart needle loops formed in one of the front and back fabric substructures and converging together in four respective plated needle loops of the pile yarns formed in a common course and wale of the other fabric substructure. In seven-bar embodiments of the fabric, each triangularly related pyramidal truss comprises six pile segments formed of a pair of pile segments of each of the three sets of pile yarns, with the six pile segments extending from six respective spaced-apart needle loops formed in one fabric substructure and converging together in six respective plated needle loops formed in a common course and wale of the other fabric substructure.

By way of example but without limitation, one set of pile yarns may be warp knitted between the front and back fabric substructures in a 1-0, 2-3, 4-5, 3-2 stitch construction, while the other pile yarns are warp knitted between the fabric substructures in a 5-4, 2-3, 0-1, 3-2 stitch construction. In an alternative embodiment, the stitch construction of the first set of pile yarns may be 1-0, 1-2, 2-3, 2-1, while the other pile yarns follow a 2-3, 2-1, 1-0, 1-2 stitch construction. In a third embodiment, one set of pile yarns is knitted in a 1-0, 2-3, 4-5, 3-2 stitch construction, while the second set of pile yarns is knitted in a 4-5, 3-2, 1-0, 2-3 stitch construction. A fourth embodiment has one set of pile yarns knitted in a 1-0, 3-4, 6-7, 4-3 stitch construction, and a second set of pile yarns in a 6-7, 4-3, 1-0, 3-4 stitch construction. In a fifth embodiment, one set of pile yarns follows a 1-0, 4-5, 8-9, 5-4 stitch construction, with the stitch construction of the second set of pile yarns being 8-9, 5-4, 1-0, 4-5. In seven-bar embodiments, the chain stitch construction of the third set of pile yarns may be a 1-0, 0-1, 0-1, 1-0 chain stitch construction or a 1-0, 0-0, 0-0, 0-1, 1-1, 1-1 chain stitch construction. As a further variation, it is also contemplated that a seven-bar embodiment of the present spacer fabric can be formed with only one set of pile yarns following a walewise alternating stitch construction while the other two sets of pile yarns follow differing chain stitch constructions.

In each presently contemplated six- or seven-bar construction of the spacer fabric, it is preferred that the same stitch construction for the front and back fabric substructures be utilized. Specifically, in one fabric substructure, the ground yarn is preferably warp knitted in an 0-1, 1-1, 3-2, 2-2 stitch construction, while the stretchable yarn is warp knitted in a 2-1, 1-1, 0-1, 1-1 stitch construction. In the other fabric substructure, the ground yarn is warp knitted in a 1-1, 3-2, 2-2, 0-1 stitch construction, while the stretchable yarn is warp knitted in a 1-1, 0-1, 1-1, 2-1 stitch construction.

It is contemplated that spacer fabrics according to the present invention will find numerous and varied applications and uses, including substantially any application or use for which neoprene, polyurethane, and like foam materials are employed. In particular, but without limitation, the present invention contemplates that especially advantageous use can be made of the present spacer fabrics as cushioning components in athletic shoes, e.g., for fabricating insoles, tongues, and sleeve-like booties integrally formed interiorly within the shoe for receiving and dynamically supporting a wearer's foot such as is utilized in the popular Hurache line of athletic shoes produced by Nike, Inc., of Beaverton, Oreg. Another advantageous application for the spacer fabric of the present invention is contemplated to be the fabrication of limb support devices such as knee, elbow and ankle braces and similar wraps for human joints and limbs for both athletic and medical applications. Of course, it should be recognized by those persons skilled in the art that the foregoing applications and uses are merely exemplary and not exhaustive. Numerous other varied uses and applications are contemplated to be within the scope of the present invention.

According to a further aspect of the process of the present invention, after knitting of the spacer fabric is completed, the spacer fabric is stretched into a predetermined stretched condition wherein the fabric retains a desired degree of residual stretchability, compressibility and resiliency while the monofilament pile yarns are substantially withdrawn interiorly into the spacer fabric from the fabric substructures and, while maintaining the fabric in the stretched condition, the fabric is heat-set to fix it dimensionally and structurally in the stretched condition. Advantageously, heat transfer printing of at least one of the fabric substructures may also be accomplished. As an alternative, one or both sets of the ground yarns may be heat transfer printed while in warp sheet form as part of the initial warp preparation process so that the resultant spacer fabric will have a desired printed pattern.

BRIEF DESCRIPTION OF THE DRAWINGS

FIG. 3 is a diagram showing individually the stitch patterns for the constituent yarns carried out by a warp knitting machine in knitting one preferred embodiment of the spacer fabric according to the method of the present invention;

FIG. 7 is a diagram similar to FIG. 1 showing individually the stitch patterns for the constituent yarns carried out by a warp knitting machine in knitting a second preferred embodiment of the present spacer fabric according to the method of the present invention;

DESCRIPTION OF THE PREFERRED EMBODIMENT

As explained more fully herein, the preferred embodiment of the fabric of the present invention is produced, and the method of the present invention is carried out, on a warp knitting machine of the conventional type commonly referred to as a double needle bar Raschel machine having two independently operated needle bars arranged back-to-back relative to one another and a plurality of yarn guide bars for feeding a corresponding number of sets of warp yarns to, and manipulating the yarns with respect to, the needle bars. The knitting machine should be of an at least six-bar construction and preferably of a seven-bar construction as will be more fully understood from the description hereinbelow. The construction and operation of such machines are well known in the warp knitting art and need not herein be specifically described and illustrated.

In the following description, the needle bars of the knitting machine are identified as "front" and "back", and the yarn guide bars of the knitting machine are numerically identified as guide bars 1, 2, 3, et seq, for reference purposes only to define the knitting relationships between the guide bars and the needle bars and not by way of limitation. As further used herein, the "bar construction" of a double needle bar Raschel warp knitting machine refers to the number of yarn guide bars of the machine, while the "bar construction" of a warp knitted fabric refers to the number of different sets of warp yarns included in the fabric, all as is conventional terminology in the art.

Figure 1:
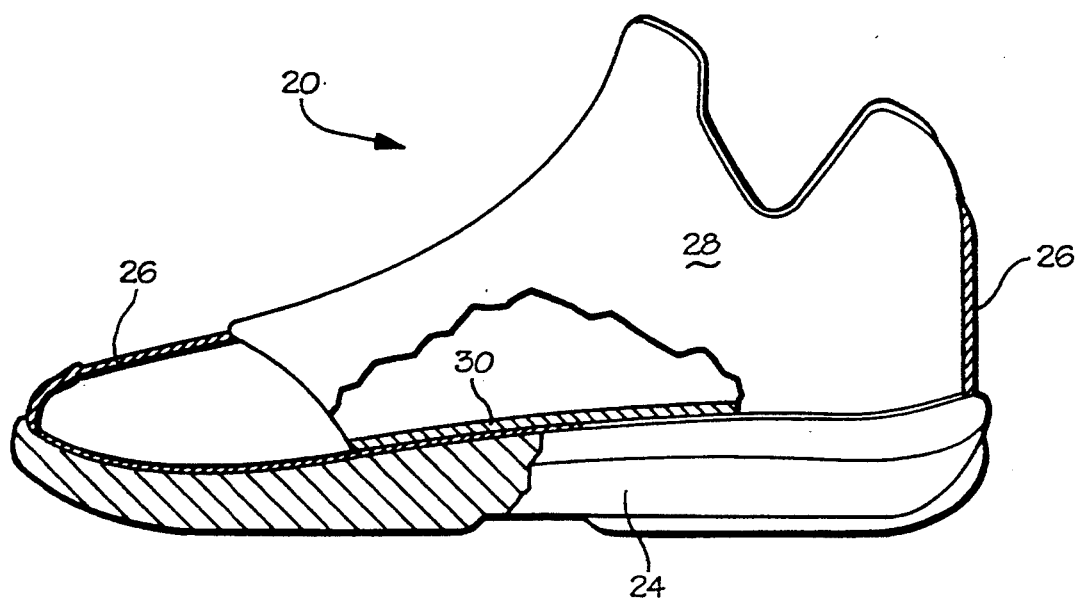
FIG. 1 is a side elevational view, partial broken away, of an athletic shoe incorporating cushioning components such as may advantageously be fabricated from the warp knitted spacer fabric of the present invention.
Figure 2:
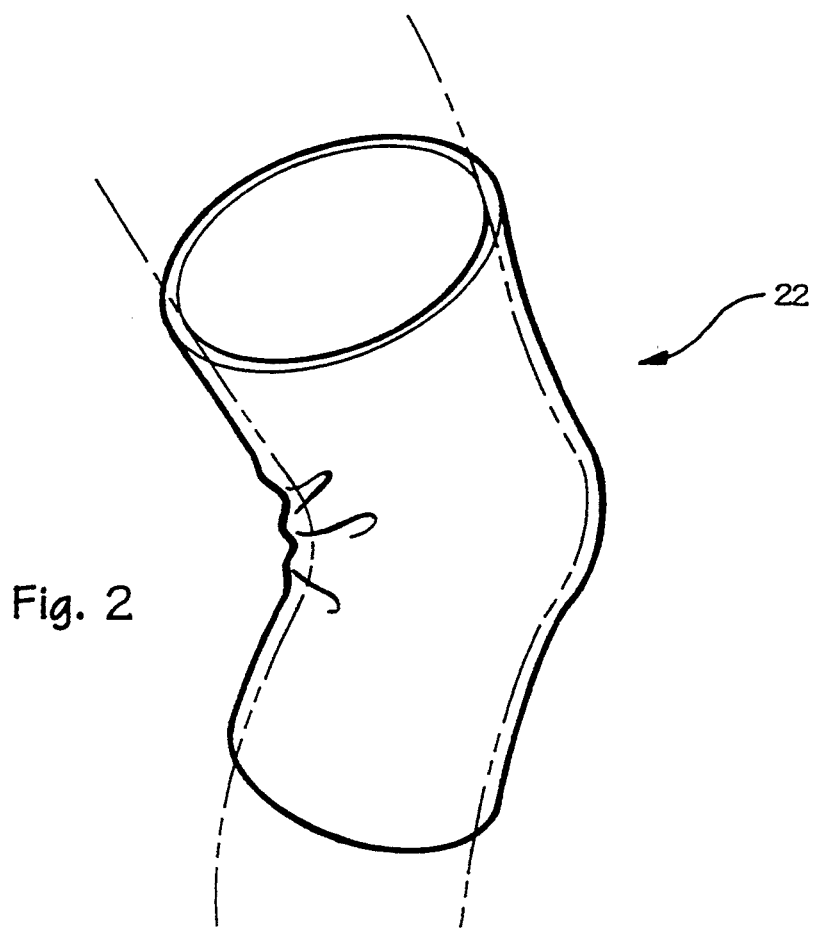
FIG. 2 is a perspective view of an athletic knee brace such as may be advantageously fabricated from the present warp knitted spacer fabric.

Referring now to the accompanying drawings and initially to FIGS. 1 and 2, an athletic shoe indicated generally at 20 in FIG. 1 and an athletic knee brace indicated generally at 22 in FIG. 2 are shown as being representative of the types of products in which warp knitted spacer fabrics according to the present invention may advantageously be utilized. The athletic shoe 20 as shown is representative of the Hurache line of athletic shoes currently manufactured and sold by Nike, Inc., of Beaverton, Oreg., and basically comprises a molded outsole 24 to which a leather or fabric shoe body or "upper" 26 is affixed adhesively and by stitching to define an interior foot pocket. A unique feature of the Hurache type of shoe is the provision of a sleeve-like bootie 28 secured within the foot pocket of the shoe to the outsole 24 and to the forward toe region of the upper 26, but otherwise being independent of the upper 26, to receive and support a wearer's foot dynamically within the outer shoe structure defined by the outsole 24 and the upper 26. A cushioned foam insole 30 is affixed in covering relation to the upwardly facing interior surface of the outsole 24 and to the stitch line along which the bootie 28 is affixed to the outsole 24.

Although the Hurache shoes have thus far proven to be relatively popular and a commercial success, a significant disadvantage and complaint of the shoes is that the bootie 28 causes excessive perspiration and overheating of the wearer's foot due to the very low air and moisture permeability of the fabric-laminated neoprene foam material from which the bootie is fabricated. This disadvantage of the Hurache athletic shoe 20 can be substantially overcome by fabrication of the sleeve-like bootie 28 from a double-needle-bar-Raschel-type warp knitted spacer fabric according to the present invention, as hereinafter more fully described. In addition, it is contemplated that the same or other embodiments of the present spacer fabric could be employed with equal advantage to fabricate the cushioned insole 30 and also to fabricate the cushioned tongue of other more traditional athletic shoes.

The knee brace 22 is representative of the conventional type fabricated in the form of a tubular sleeve formed of a conventional laminate material having a neoprene or other foam core layer with a fabric covering adhesively secured to the opposite surfaces of the core. While the stretchability, compressibility and resiliency of this fabric-backed neoprene laminate material is well suited to the intended function of the knee brace 22 in providing supplementary support to the wearer's knee against undesired twisting and other abnormal movements, knee braces fabricated of such materials suffer the same disadvantage and complaints of producing excessive perspiration and overheating as mentioned above. Thus, hereagain, a warp knitted spacer fabric in accordance with the present invention can be produced to provide comparable physical characteristics of stretchability, resiliency and compressibility to that of the fabric-backed neoprene laminate so as to equally serve the intended joint support function of the knee brace 22, but with substantially enhanced air and moisture permeability.

With reference now to FIG. 3, one particular embodiment of the present spacer fabric is illustrated as preferably warp knitted of a six-bar construction on a conventional double needle bar Raschel warp knitting machine equipped with six or preferably seven yarn guide bars, in accordance with the present method. As is conventional, each needle bar of the knitting machine carries a series of aligned knitting needles, while each guide bar of the machine carries a series of guide eyes, the needle and guide bars typically having the same gauge, i.e., the same number of needles and guide eyes per inch. According to the present invention, the Raschel machine should be of a relatively fine gauge, preferably 20 needles per inch or greater.

According to the embodiment of the present fabric diagrammatically represented in FIG. 3, six of the seven yarn guide bars are employed, with each of guide bars 1 and 7 fully threaded on every guide member with respective sets of stretchable elastic ground yarns 32,42 delivered from respective warp beams (not shown), each of guide bars 2 and 6 fully threaded on every guide member with respective sets of ground yarns 34,40 delivered from other respective warp beams (also not shown), and guide bars 3 and 5 similarly fully threaded on every guide member with respective sets of pile yarns 36,38 supplied from two additional warp beams (also not shown). Guide bar 4 in this embodiment is left empty.

It is contemplated that a variety of yarns may be suitable for use as the ground and pile yarns. For example, any of a variety of conventional multi-filament synthetic yarns, particularly polyester yarns, would be suitable for use as either or both the ground yarns 34,40. Texturized yarns offer the additional advantage of enhancing the desired stretchability of the fabric. Likewise, any of a variety of conventional stretchable synthetic yarns are suitable for use as either or both of the stretchable ground yarns 32,42, an elastomeric yarn such as Lycra brand yarn produced by E. I. dupont de Nemours and Company of Wilmington, Del., being preferred. The pile yarns 36,38 preferably should be relatively more stiff than the ground yarns yet sufficiently flexible and resilient to optimize the desired properties of compressibility and resiliency of the spacer fabric across its thickness dimension, but without detracting from the hand and feel of the outward surfaces of the spacer fabric. For this purpose, monofilament polyester yarns are preferred. The denier of the ground and pile yarns may vary depending upon the desired weight, hand/feel, and intended end use of the spacer fabric, but in most cases in which the fabric may have apparel or other bodywear application, the monofilament pile yarns are preferably of relatively fine denier, e.g., in the range of 40 denier and less and, more preferably, 30 denier and less, to minimize the effect of the monofilament yarns on the hand and feel of the fabric.

In the accompanying FIG. 3, the stitch constructions of the ground and pile yarns 32,34,36,38,40,42, as carried out by the respective lateral traversing movements of the guide bars of the knitting machine according to one possible embodiment of the present fabric and method, are illustrated individually in a traditional dot or point diagram format, wherein the individual points 44 in the alternating horizontal rows F represent the needles of the "front" needle bar of the knitting machine in the formation of several successive fabric courses C across several successive fabric wales W of the front fabric substructure of the spacer fabric and the individual points 46 in the intervening horizontal rows B of points represent the needles of the "back" needle bar of the knitting machine in the formation of several successive fabric courses C across several successive fabric wales W of the back fabric substructure of the spacer fabric.

According to this embodiment, guide bars 1 and 2 feed their respective sets of ground yarns 32,34 exclusively to the needles 44 of the "front" needle bar F and, likewise, guide bars 6 and 7 feed their respective ground yarns 40,42 exclusively to the needles 46 of the "back" needle bar B. Guide bars 3 and 5 respectively feed the monofilament pile yarns 36,38 alternately back and forth between the needles 44,46 of the front and back guide bars F,B in the formation of successive fabric courses C of both front and back fabric substructures.

More specifically, guide bar 1 of the warp knitting machine manipulates the set of stretchable elastic ground yarns 32 as they are fed from their respective warp beam to traverse laterally back and forth relative to the front needle bar of the knitting machine to stitch the yarns 32 on every needle 44 during the formation of every course C of the "front" fabric substructure in a repeating 2-1, 1-1, 0-1, 1-1 stitch pattern. Similarly, guide bar 2 simultaneously manipulates the set of ground yarns 34 as they are fed from their respective warp beam to traverse relative to the front needle bar to stitch the ground yarns 34 on every front needle 44 during the formation of each successive course C of the "front" fabric substructure in a repeating 0-1, 1-1, 3-2, 2-2 stitch pattern. Simultaneously, guide bar 7 manipulates the set of stretchable elastic ground yarns 42 as they are fed from their respective warp beam to traverse relative to the back needle bar to stitch the yarns 42 on every needle of the back needle bar during the formation of each successive course C of the "back" fabric substructure in a repeating 1-1, 0-1, 1-1, 2-1 stitch pattern, while guide bar 6 manipulates the set of ground yarns 40 as they are fed from their respective warp beam to traverse relative to the back needle bar to stitch the yarns 40 on every back needle during the formation of each successive course C of the "back" fabric substructure in a repeating 1-1, 3-2, 2-2, 0-1 stitch pattern.

As the above-described movements of guide bars 1,2,6,7 are carried out, guide bar 3 manipulates the set of monofilament pile yarns 36 as they are fed from their respective warp beam to traverse relative to both the front and back needle bars F,B to stitch the yarns 36 alternately on the front needles 44 and then on the back needles 46 during the successive formation of corresponding courses C of the front and back fabric substructures in a repeating 1-0, 2-3, 4-5, 3-2 stitch pattern, while guide bar 5 operates essentially in reverse of guide bar 3 to manipulate the set of pile yarns 38 as they are fed from their respective warp beam to traverse relative to both the front and back needle bars F,B to stitch the yarns 38 alternately on the back needles 46 and the front needles 44 during the successive formation of corresponding courses C of the front and back fabric substructures in a repeating 5-4, 2-3, 0-1, 3-2 stitch pattern.

As will thus be understood, the ground and pile yarns 32,34,36,38 are interknitted with one another in the front fabric substructure by the formation of respective plated needles loops 32n,34n,36n,38n of the yarns in every wale W of every course C of the front fabric substructure, while similarly the pile and ground yarns 36,38,40,42 are interknitted with one another in the back fabric substructure by formation of respective needle loops 36n',38n',40n,42n of the yarns in every wale W of every course C of the back fabric substructure, with the segments 36s,38s of the pile yarns 36,38 extending between their respective successive needle loops in the front and back fabric substructures connecting the two fabric substructures in substantially parallel spaced relation.

Figure 4:
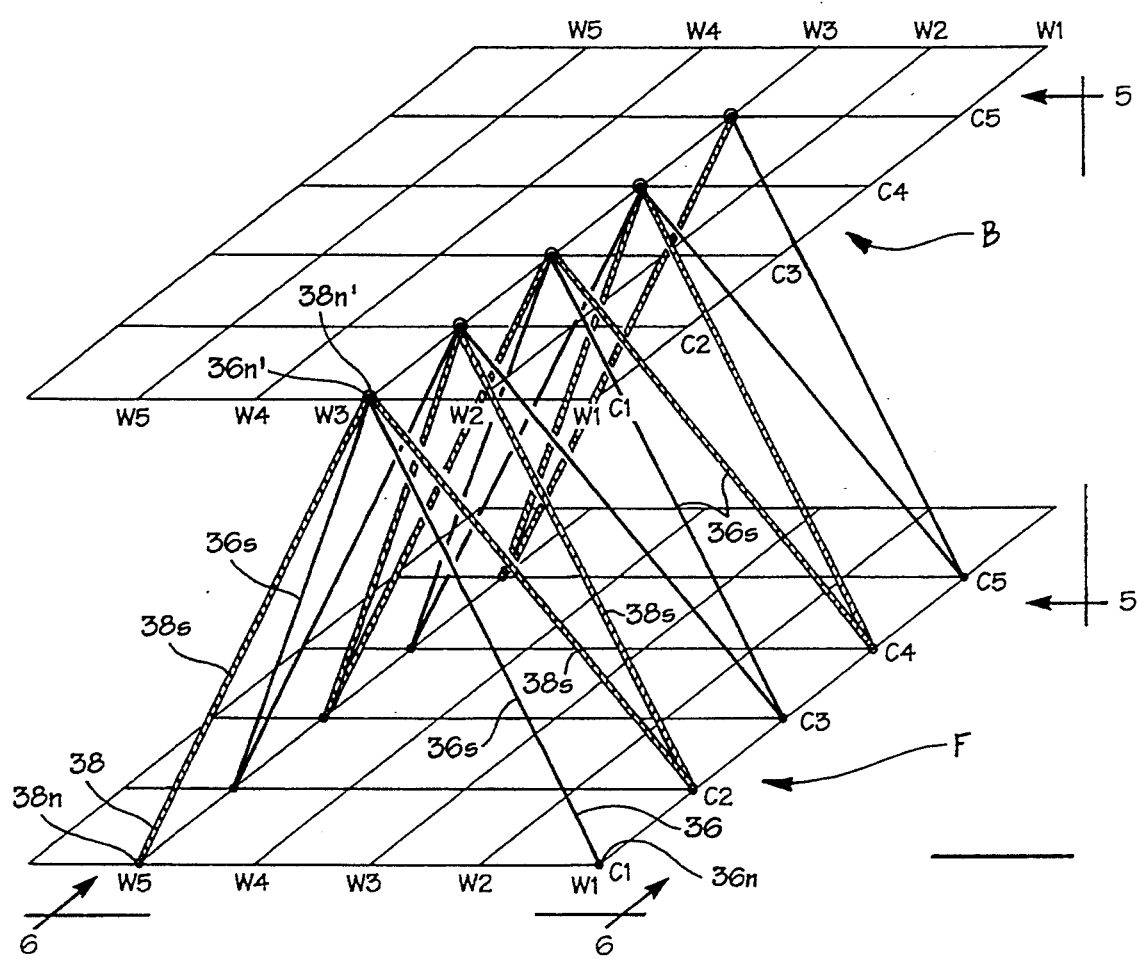
FIG. 4 is a schematic perspective view of the pile substructure of the spacer fabric represented in the diagram of FIG. 3.
Figure 5:
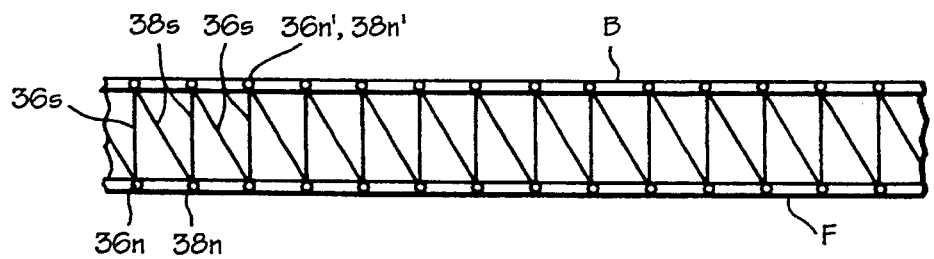
FIG. 5 is a schematic cross-sectional view of the spacer fabric of FIGS. 3 and 4, as viewed taken along lines 5—5 of FIG. 4.
Figure 6:
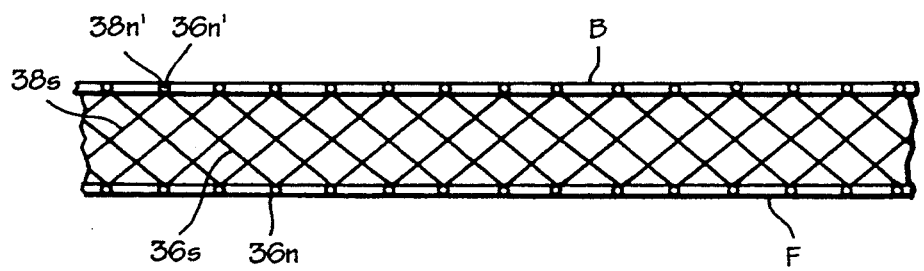
FIG. 6 is another schematic cross-sectional view of the spacer fabric of FIGS. 3 and 4, as viewed taken along lines 6—6 of FIG. 4.

As will therefore be understood and as best depicted in FIGS. 4, 5 and 6, the respective stitch constructions of the pile yarns 36,38 cause each pile yarn of each set to be formed in successive needle loops which alternate every course between non-corresponding wales of the front and back fabric substructures F,B. More specifically, the successive needle loops 36n,36n' of each pile yarn 36 and the successive needle loops 38n,38n' of each pile yarn 38 are knitted alternatingly but in mirror-image relation to one another in alternate needle loops 36n,38n formed in each successive course of the front fabric substructure F alternatingly between spaced-apart wales which are separated from one another by three intervening wales and in intervening needle loops 36n',38n' formed in a common wale of each successive course of the back fabric substructure B.

This stitch construction of the pile yarns 36,38 is schematically depicted in three-dimensional perspective in FIG. 4 wherein a single pile yarn 36 and a single pile yarn 38 are shown to be knitted in needle loops 36n,38n, represented only by dots in the drawing, alternating each successive course C1, C2, C3, et seq, of the front fabric substructure F between spaced-apart wales W1,W5 and in plated intervening needle loops 36n',38n', again represented only by dots, formed in the single common wale W3 of each successive course C1, C2, C3, et seq, of the back fabric substructure B. As will be readily understood from the schematic illustration of FIG. 4, the respective stitch constructions of the pile yarns 36,38 cause the pile yarn segments 36s,38s to extend angularly transversely back and forth between the front and back fabric substructures F,B to collectively form a series of truss-like pyramidal yarn supports each comprised of two pile yarn segments 36s and two pile yarn segments 38s extending from four spaced-apart needle loops 36n,38n in the front fabric substructure F to four plated needle loops 36n',38n' in the back fabric substructure B. This pyramidal truss system of the pile yarn segments serves to maintain the fabric substructures F,B in spaced parallel relation yet is sufficiently resiliently yieldable for a desired degree of compressibility of the spacer fabric across its thickness dimension. Of course, as will be understood by persons skilled in the art, since guide bars 3 and 5 which carry the pile yarns 36,38 are fully threaded through each guide eye with the pile yarns, each other corresponding pair of pile yarns 36,38 fed by the guide bars 3 and 5 would cooperate to form a similar pyramidal support arrangement of yarn segments 36s,38s so as to occupy every wale of the fabric substructures F,B, only a single pile yarn 36 and a single pile yarn 38 being shown in FIG. 4 for sake of clarity.

FIGS. 5 and 6 schematically depict walewise and coursewise cross-sections of the spacer fabric construction of FIG. 4 to diagrammatically show the overall pyramidal arrangement of yarn segments 36s,38s collectively formed by all of the pile yarns 36,38. Advantageously, this pyramidal arrangement of the pile yarn segments 36s,38s acts in the nature of a system of triangularly-related trusses which support and maintain the front and back fabric substructures in spaced parallel relation and also resist relative shear movement of the fabric substructures when subjected to forces exerted in directions generally parallel to the fabric substructures, while also providing resilient compressibility to the spacer fabric as mentioned.

As those persons skilled in the art will readily recognize and understand, the spacer fabric construction and fabrication method of the present invention is susceptible of a number of variations which will also produce the preferred pyramidal support construction of the pile yarn substructure of the fabric. As presently contemplated, it is believed that seven-bar constructions of the spacer fabric of this invention wherein a third set of pile yarns is utilized will provide additionally enhanced properties of resiliency, compressibility and shear resistance to the present spacer fabric. One representative example of a contemplated seven-bar spacer fabric construction is represented diagrammatically and schematically in FIGS. 7-10. In similar fashion to FIG. 3, FIG. 7 depicts the stitch constructions of the ground and pile yarns of this spacer fabric as carried out by the respective lateral traversing movements of the guide bars of the Raschel knitting machine in the same form of traditional point diagram shown in FIG. 3.

As will be recognized, guide bars 1,2,6,7 are employed in this spacer fabric construction to knit stretchable and ground yarns 32,34,40,42 exclusively on the front and back needle bars 44,46, respectively, according to the identical repeating stitch patterns of the spacer fabric of FIG. 3. However, in contrast to the fabric of FIG. 3, three sets of pile yarns 136,138,139 are fed respectively by the three middle guide bars 3,4,5 back and forth between the front and back needle bars 44,46 in the formation of successive courses C of the front and back fabric substructures F,B. Each of guide bars 3,4,5 is fully threaded on every guide bar with its respective set of pile yarns. As depicted, in this embodiment, guide bar 3 operates to stitch the pile yarns 136 alternately between the front and back needles 44,46 during the formation of successive courses of the front and back fabric substructures F,B in a repeating 1-0, 1-2, 2-3, 2-1 stitch pattern. Guide bar 4 operates in essentially mirror-image relation to guide bar 3 to stitch the pile yarns 138 alternately between the front and back needles 44,46 during the formation of successive courses of the front and back fabric substructures F,B in a repeating 2-3, 2-1, 1-0, 1-2 stitch pattern. In addition, guide bar 5 in this embodiment stitches each pile yarn 139 alternatingly between the front and back needles 44,46 in the formation of successive courses of the front and back fabric substructures F,B in a repeating 1-0, 0-1, 0-1, 1-0 chain stitch pattern.

Figure 8:
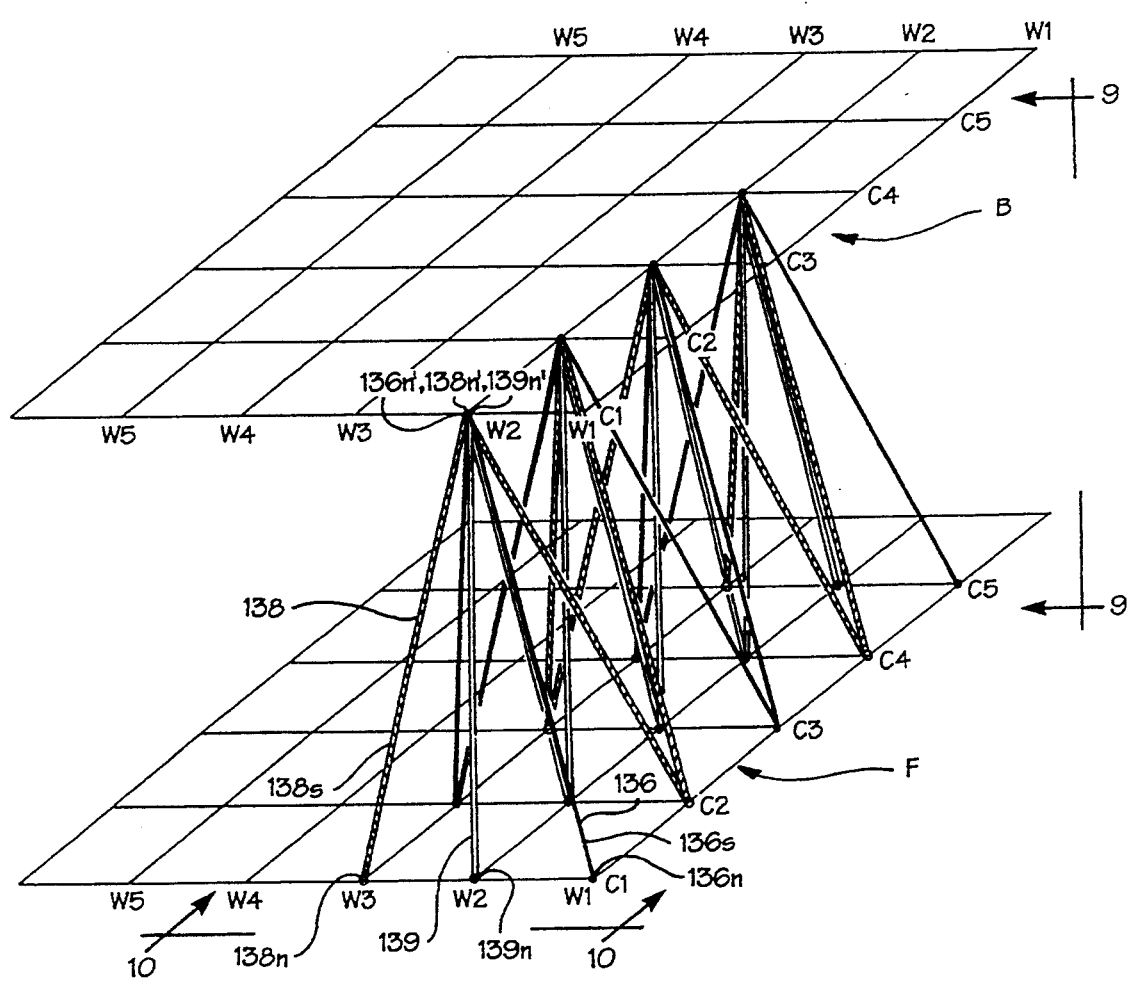
FIG. 8 is a schematic perspective view similar to FIG. 4 depicting the pile substructure of the spacer fabric represented by the diagram of FIG. 7.

Thus, as depicted in FIG. 8, wherein as with FIG. 4 only a single pile yarn 136, a single pile yarn 138, and a single pile yarn 139 is shown for sake of clarity, the stitch construction of each pile yarn 136 produces a succession of needle loops formed in alternating needle loops 136$n$ appearing in each successive course C1, C2, C3, et seq, of the front fabric substructure F alternatingly between spaced-apart wales, e.g., wales W1,W3, separated by a single intervening wale, e.g., wale W2, and in intervening needle loops 136$n'$ formed in each successive course C1, C2, C3, et seq, of the back fabric substructure B in a common wale, e.g., wale W2. In essentially mirror-image relation, successive needle loops of each pile yarn 138 are formed in alternating needle loops 138$n$ appearing in each successive course C1, C2, C3, et seq, of the front fabric substructure F alternatingly at the same walewise spacing, e.g., wales W1,W3, and in intervening needle loops 138$n'$ formed in a common wale, e.g., wale W2, of each successive course C1,C2,C3 of the back fabric substructure. The pile yarns 139 are chain stitched in a succession of needle loops 139$n$,139$n'$ wherein the alternating needle loops 139$n$ are formed in each successive course C1,C2,C3 of the front fabric substructure F in a common wale, e.g., wale W2, with the intervening needle loops 139$n'$ similarly appearing in each successive course C1,C2,C3 of the back fabric substructure B in a common wale, e.g., wale W2, which directly corresponds to the wale of the front fabric substructure occupied by the needle loops 139$n$.

Figure 9:
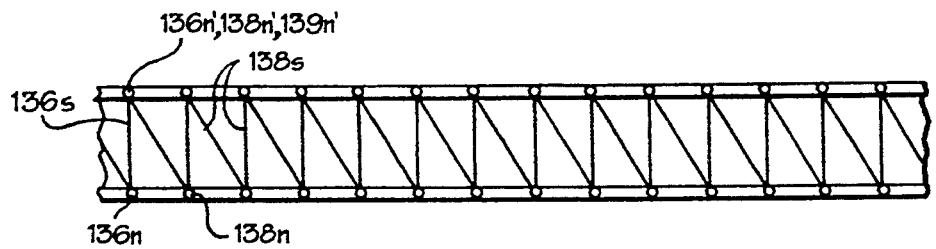
FIG. 9 is a schematic cross-sectional view of the spacer fabric of FIGS. 7 and 8, as viewed taken along line 9—9 of FIG. 8.
Figure 10:
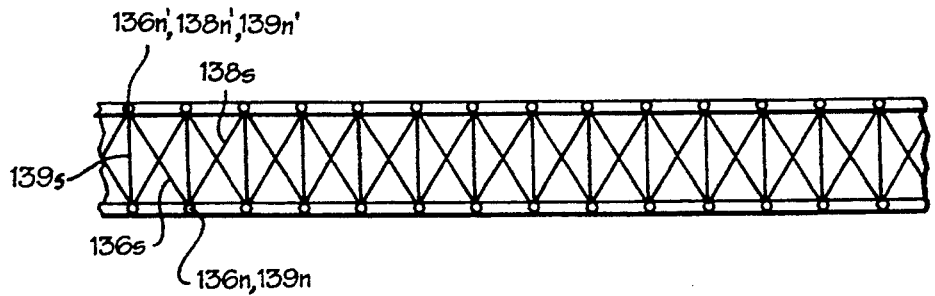
FIG. 10 is another schematic cross-sectional view of the spacer fabric of FIGS. 7 and 8, as viewed taken along line 10—10 of FIG. 8.

As will thus be understood, the respective stitch constructions of the pile yarns 136,138,139 in the spacer fabric of FIGS. 7 and 8 produces a similar pyramidal arrangement of the segments 136$s$,138$s$,139$s$ of the pile yarns 136,138,139, respectively, extending back and forth between the front and back fabric substructures F,B, producing a similar system of triangularly related pyramidal trusses formed collectively by the pile yarn segments. In contrast to the spacer fabric of FIGS. 3 and 4, however, each pyramidal arrangement of the pile yarn segments 136$s$,138$s$,139$s$ is formed by six pile segments comprised of a pair of pile yarn segments 136$s$, a pair of pile yarn segments 138$s$, and a pair of pile yarn segments 139$s$, with the six pile yarn segments extending from six respective spaced-apart needle loops 136$n$,138$n$,139$n$ formed in the front fabric substructure F and converging together in six respective plated needle loops 136$n'$,138$n'$,139$n'$ formed in a common course and wale of the back fabric substructure B, all as will be best seen and understood with reference to the schematic diagram of FIG. 8. FIGS. 9 and 10 schematically show the spacer fabric of FIGS. 7 and 8 in walewise and coursewise cross-sections, similar to the illustrations of FIGS. 5 and 6.

As will thus be seen, the respective stitch constructions of the pile yarns 136,138,139 produce a pyramidal arrangement wherein the pile yarn segments 136$s$,138$s$,139$s$ in the spacer fabric of FIGS. 7 and 8 are shorter than in the spacer fabric of FIGS. 3 and 4, which produces a slightly lesser thickness to the spacer fabric of FIGS. 7 and 8 and, together with the addition of the third set of pile yarns 139, provides the spacer fabric of FIGS. 7 and 8 with a greater degree of resistance to compression in the thickness dimension of the fabric but also enhanced resiliency and recovery from compression. In addition, the formation of each pyramidal arrangement of pile yarn segments from three collective pairs of the pile yarn segments 136$s$,138$s$,139$s$ provides the distinct advantage of investing the spacer fabric with further enhanced resistance to shear forces imposed on the two fabric substructures F,B. The net result is that the spacer fabric of FIGS. 7 and 8 closely approximates the physical and functional properties of conventional fabric-backed neoprene laminate materials such as utilized in the athletic shoe 20 and the knee brace 22 of FIGS. 1 and 2.

By way of further example, additional contemplated embodiments of seven-bar spacer fabrics in accordance with the present invention are depicted in FIGS. 11-17. As with the spacer fabrics of FIGS. 3 and 7, each guide bar of the double needle bar Raschel knitting machine is fully threaded with its respective set of yarns extending through every guide eye of the guide bar. Likewise, the stretchable elastic and ground yarns 32,34,40,42 are manipulated by the respective guide bars 1,2,6,7 on the respective front and back needle bars 44,46 identically to the stitch patterns of the respective yarns as already described above in the embodiments of FIGS. 3 and 7. Thus, the additional embodiments of FIGS. 11-17 differ from one another solely with respect to the stitch patterns followed by the three middle guide bars 3,4,5 through which the three sets of pile yarns 136,138,139 are fed to the needle bars 44,46.

Figure 11:
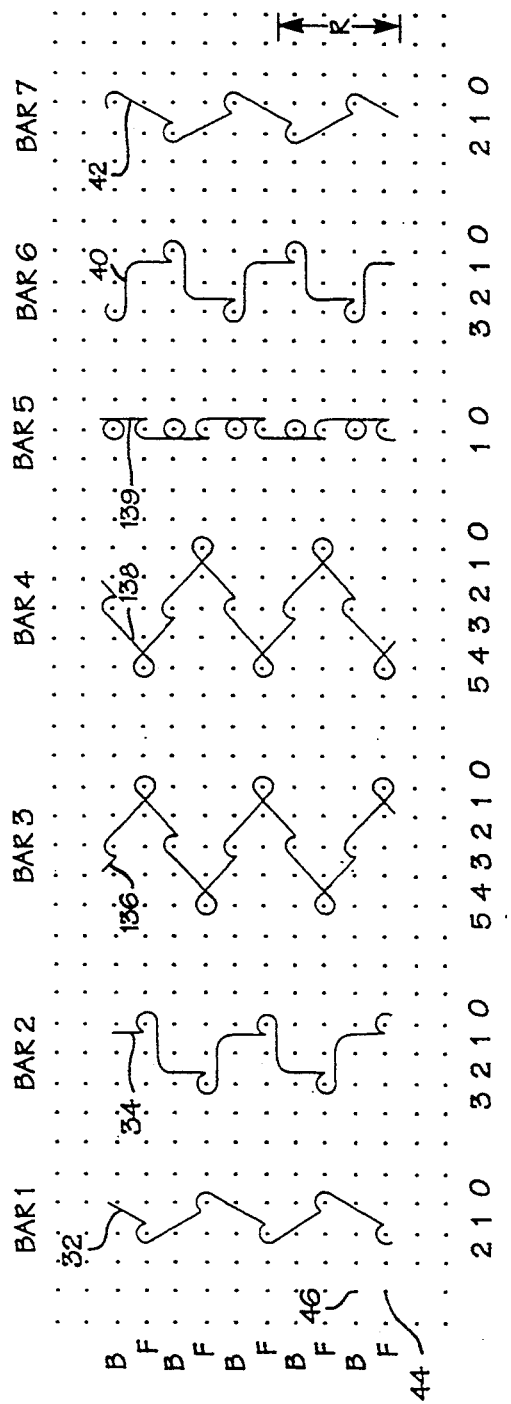
FIGS. 11-17 are further diagrams similar to FIGS. 3 and 7 showing individually the stitch patterns for the constituent yarns carried out by a warp knitting machine in knitting additional contemplated embodiments of the present spacer fabric according to the method of the present invention.
Figure 12:
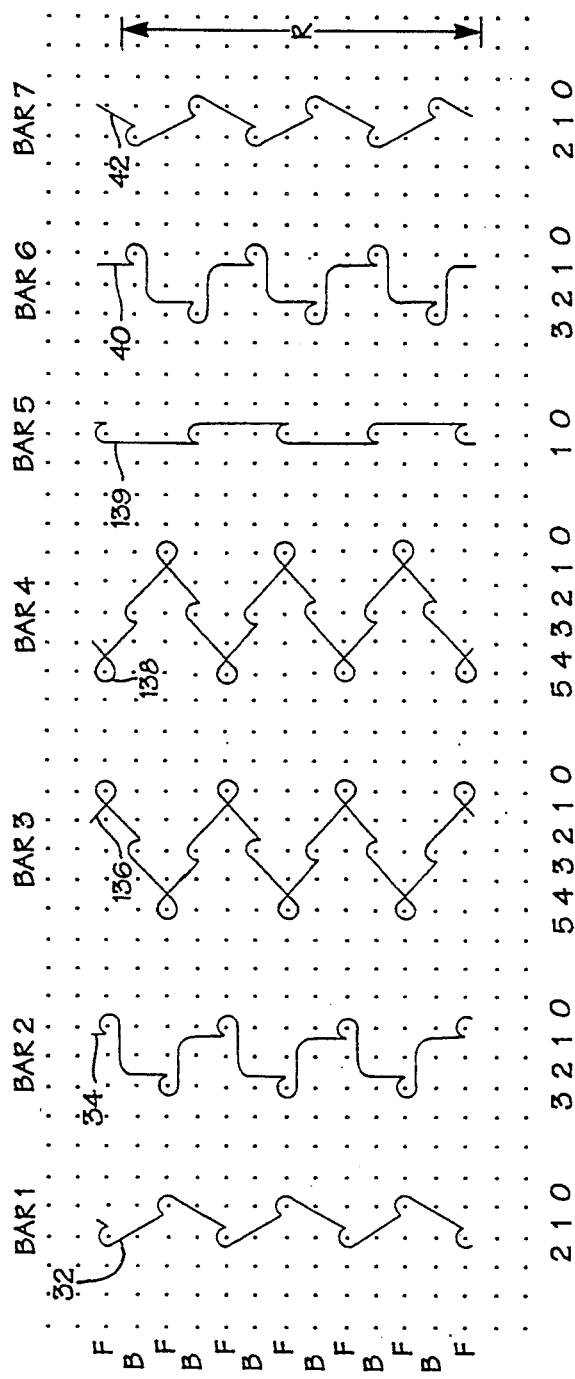

Specifically, FIG. 11 depicts diagrammatically a seven-bar spacer fabric substantially comparable to that of FIG. 7, with bar 5 stitching the pile yarns 139 in the identical chain stitch construction as FIG. 7, but with bar 3 stitching the pile yarns 136 in a repeating 1-0, 2-3, 4-5, 3-2 stitch pattern and bar 4 stitching the pile yarns 138 in a repeating 4-5, 3-2, 1-0, 2-3 stitch pattern similar to the yarns 36,38 of FIG. 3. The seven-bar spacer fabric of FIG. 12 has the pile yarns 136,138 knitted in the identical stitch pattern as in the fabric of FIG. 11, but with the pile yarns 139 following a different 1-0, 0-0, 0-0, 0-1, 1-1, 1-1 chain stitch pattern, whereby the overall fabric pattern repeat occurs every six courses of the front and back fabric substructures F,B rather than every two courses as in each of the preceding embodiments hereinabove described.

Figure 13:
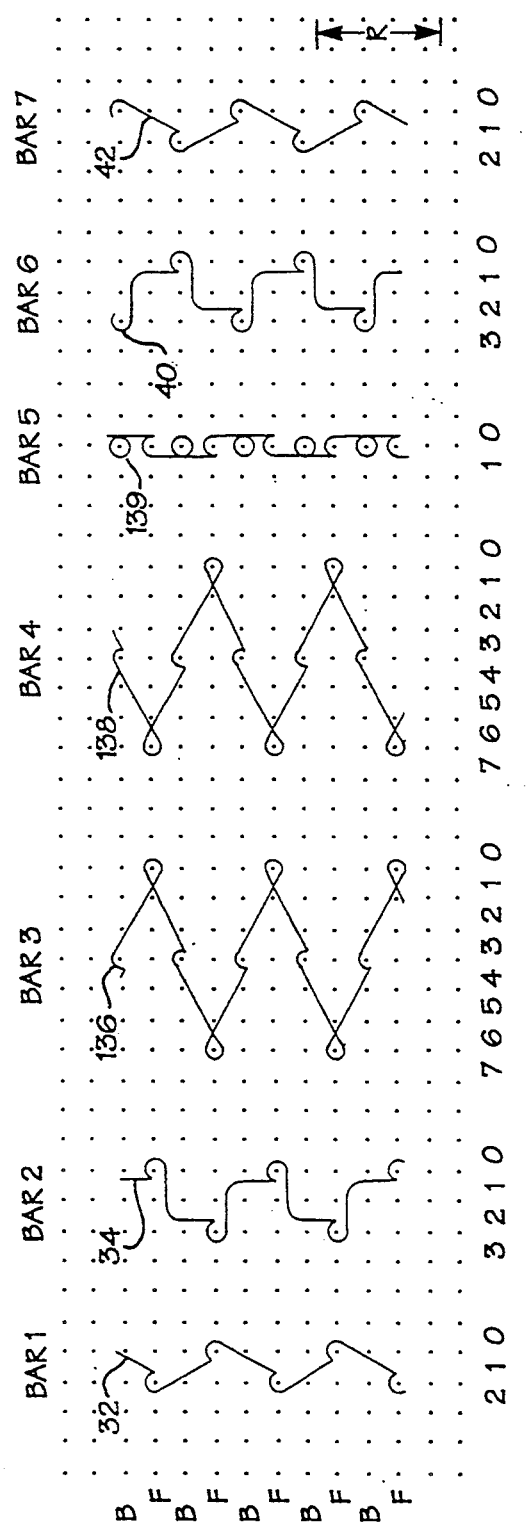

The seven-bar spacer fabric of FIG. 13 corresponds to that of FIGS. 7 and 11 except that the pile yarns 136 are knitted in a 1-0, 3-4, 6-7, 4-3 stitch pattern and the pile yarns 138 are knitted in a 6-7, 4-3, 1-0, 3-4 stitch pattern thereby producing a greater spacing between the successive needle loops of these pile yarns and, in turn, investing the spacer fabric with a greater thickness. The spacer fabric of FIG. 14 is identical to FIG. 13 except that the pile yarns 139 follow the chain stitch pattern of the fabric of FIG. 12.

Figure 14:
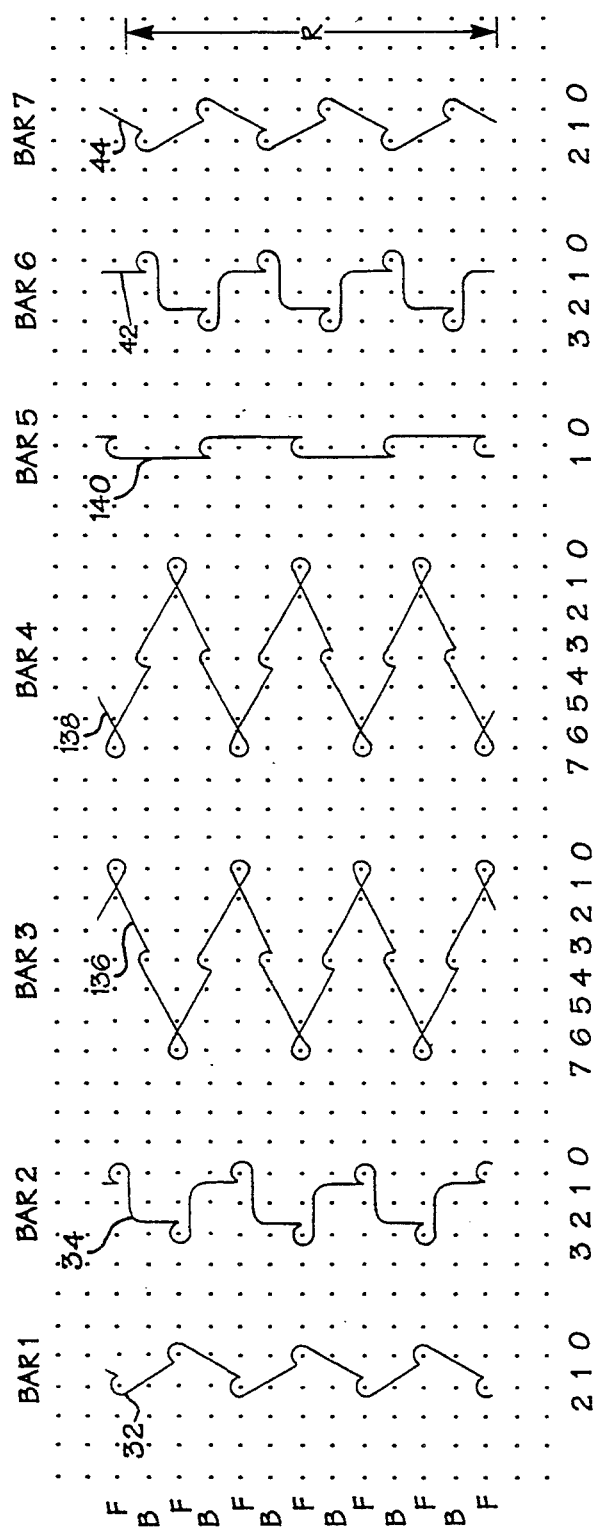
Figure 15:
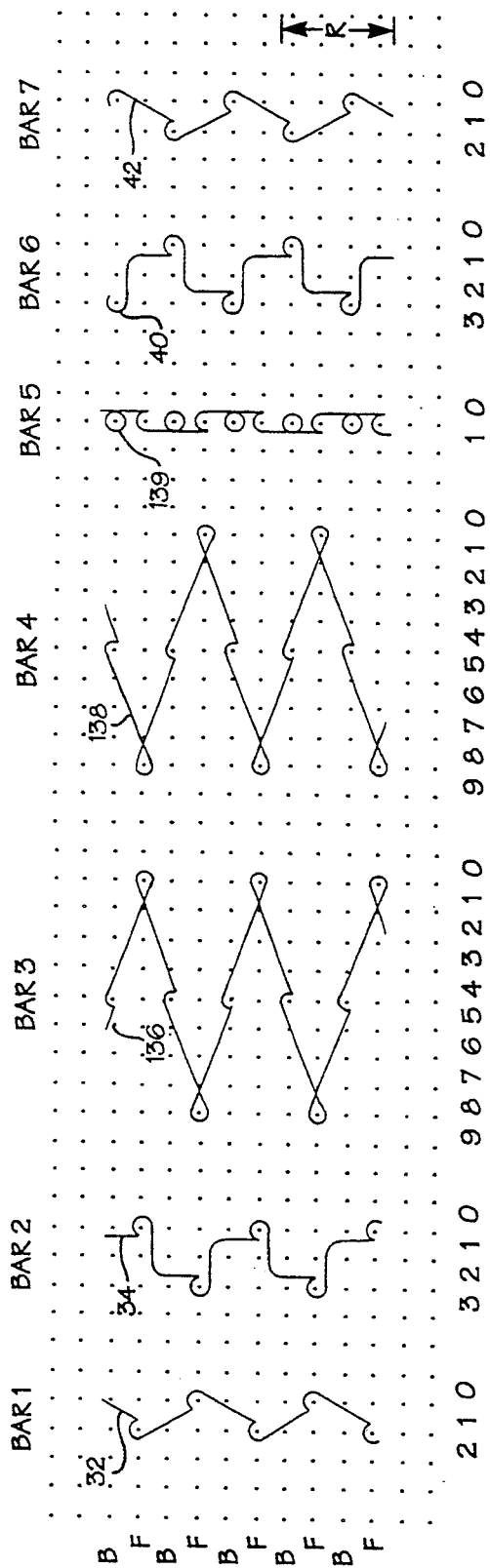
Figure 16:
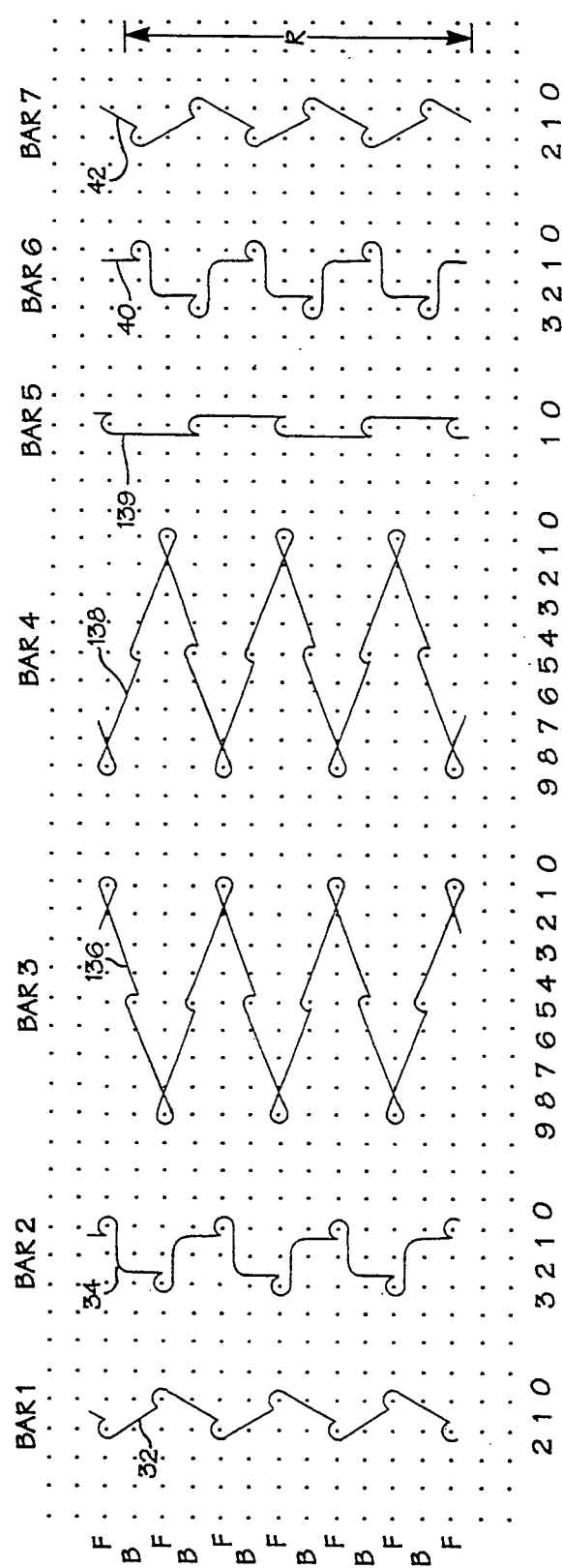

The spacer fabrics of FIGS. 15 and 16 correspond to those of FIGS. 13 and 14 except that guide bar 3 knits the pile yarns 136 in a 1-0, 4-5, 8-9, 5-4 stitch pattern and guide bar 4 knits the pile yarns 138 in an 8-9, 5-4, 1-0, 4-5 stitch pattern to form the spacer fabric of an even greater thickness.

Figure 17:
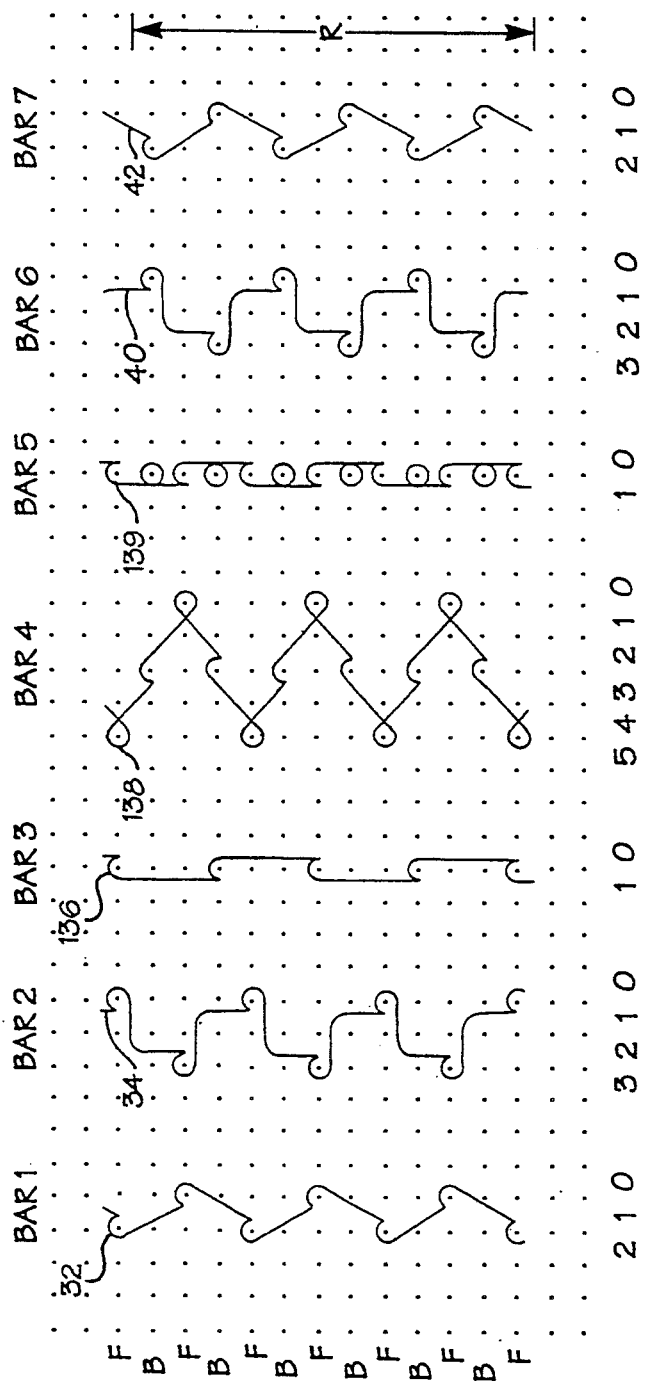

In contrast to the spacer fabric constructions of FIGS. 3, 7 and 11-16 described above, the seven-bar spacer fabric embodiment of FIG. 17 utilizes only one of the three middle guide bars, i.e., guide bar 4, to knit one corresponding set of the pile yarns, i.e., pile yarns 138, in a stitch pattern causing the successive needle loops of the pile yarn to alternate between spaced wales of successive courses in the front and back fabric substructures F,B, the guide bar 4 knitting the pile yarns 138 in a repeating 4-5, 3-2, 1-0, 2-3 stitch pattern. The other two middle guide bars 3,5 stitch their respective pile yarns 136,139 in the two differing chain stitch patterns utilized in the several above-described seven-bar fabric embodiments of FIGS. 7 and 11–16.

As will thus be understood, each of the various described embodiments of the spacer fabric of the present invention accomplishes a pyramidal arrangement of the segments of the pile yarns which extend between the front and back fabric substructures F,B so that the pile yarn segments act in the nature of a system of triangularly related trusses extending transversely between the opposing fabric substructures F,B in differing angular orientations relative to the widthwise and lengthwise dimensions of the spacer fabric. As a result, in each embodiment, the system of two or three sets of pile yarns serves to maintain the front and back fabric substructures F,B in spaced parallel relation to provide a desired degree of thickness to the fabric while also being resiliently yieldable in the thickness dimension of the fabric to provide a resiliently compressible character simulative and comparable to that of conventional foam materials such as neoprene and polyurethane.

As will be apparent from the above description of various contemplated embodiments of this invention, the desired thickness of the present spacer fabric can be controlled by selection of the particular stitch construction used for the pile yarns, more specifically by increasing or decreasing the number of needles and, in turn, the number of wales across which the pile yarns lap back and forth between the formation of successive pile yarn needle loops. Those persons skilled in the art will also recognize that the thickness of the spacer fabric can be controlled additionally or alternatively by adjusting the trick plate of the Raschel machine to set the spacing between the front and back needle bars. By these adjustments, the present spacer fabric can be selectively formed of thicknesses varying between approximately 2-3 millimeters and approximately 12-14 millimeters.

In addition, the stitch constructions of the pile yarns in cooperation with the stitch constructions of the stretchable and ground yarns in the opposing front and back substructures provide the spacer fabrics of the present invention with properties of stretchability, modulus and power comparable to that of conventional foam materials. At the same time, the spacer fabrics of the present invention exhibit substantially enhanced air and moisture permeability over the largely impermeable conventional foam materials mentioned. Finally, the pyramidal truss-like structure of the collective pile yarns in the spacer fabrics of the present invention and, particularly, the differing angular orientations assumed by the individual pile yarn segments, especially in seven bar embodiments, gives the present spacer fabrics improved resistance to relative shear movement of the fabric substructures in directions parallel to their length and width dimensions even in relatively thick embodiments of the present spacer fabric, in substantial contrast to known spacer fabric constructions wherein disadvantageous shear effects tend to increase significantly with increases in the fabric thickness.

In addition to the Raschel warp knitting methodology of the present invention described above, the process of producing the present spacer fabrics in accordance with the present invention also contemplates several possible post-knitting steps which enable physical and aesthetic properties of the spacer fabrics to be selectively engineered. Specifically, it is known that double needle bar Raschel spacer fabrics undergo a relatively significant coursewise loss of width in the relaxed fabric upon removal from the knitting machine in comparison to the widthwise dimension of the fabric while held constrained on the needle bars of the machine during knitting. For example, a spacer fabric produced on a Raschel knitting machine having a 65-inch operating width of its needle bars may assume a relaxed width of only about 35 inches after removal from the machine, representing almost a fifty percent loss in width. While it is of course possible and desirable in some circumstances to utilize such spacer fabrics in this relaxed knitted state, the process of the present invention also contemplates the possibility of subjecting any of the spacer fabrics of the present invention to a subsequent heat setting process wherein the spacer fabric, after knitting and removal from the knitting machine, is stretched to a predetermined condition, usually in the range of about twenty percent from the relaxed condition of the fabric as withdrawn from the knitting machine and then, while maintaining the spacer fabric in the stretched condition, the fabric is heat set to fix it dimensionally and structurally in its stretched condition.

By heat setting the fabric in a desired stretched condition, the spacer fabric can be selectively engineered to retain a desired degree of residual stretchability, compressibility and resiliency and its final dimensional thickness and width can also be selectively determined. An additional advantage is that the monofilament pile yarns, under the influence of the stretching forces imposed, are caused to substantially withdraw interiorly into the spacer fabric structure and thereby minimize the appearance of their needle loops at the outward surfaces of the fabric, thereby improving the hand and feel of the fabric.

An additional advantage of the present spacer fabric is the possibility of heat transfer dyeing of one or both of the front and back fabric substructures, providing the ability to independently dye one or both faces of the surface fabric with any desired printed pattern. As an alternative, or in addition, the ground yarns forming the front and back fabric substructures can be heat transfer printed or dyed in warp sheet form during the preliminary warp preparation process prior to knitting to achieve a desired pattern in the resultant knitted fabric. Advantageously, the heat setting process has been found to improve the dye or print intensity of appearance in the fabric substructures due to the lesser outward appearance of the monofilament pile yarns at the fabric faces.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. A warp knitted textile spacer fabric of the double needle bar Raschel pile type having characteristics of stretchability, compressibility and resiliency simulative of resilient plastic foam materials and having characteristics of air and moisture permeability substantially enhanced over said foam materials, said spacer fabric comprising front and back stretchable fabric substructures and a pile substructure integrated with and extending between the front and back fabric substructures for maintaining the front and back fabric substructures in spaced parallel relation and being resiliently yieldable for compressibility of the front and back fabric substructures together and subsequent recovery thereof to spaced parallel relation, said spacer fabric being of an at least six-bar warp knitted Raschel construction wherein each said fabric substructure comprises at least a set of ground yarns and a set of stretchable yarns interknitted with one another in a stretchable resilient stitch construction having needle loops of said ground and stretchable yarns arranged in longitudinal wales and transverse courses and said pile substructure comprises at least two sets of monofilament pile yarns interknitted with each said fabric substructure in a stitch construction forming pile segments which extend transversely between said fabric substructures in differing angular orientations relative thereto for permitting resilient compressibility of said fabric substructures while resisting relative shear movement of said fabric substructures in directions parallel thereto, each pile yarn of at least one of said two sets of pile yarns being formed in successive needle loops which alternate every course between non-corresponding wales of said front and back fabric substructures including alternating needle loops formed alternatingly in spaced wales of successive courses of one of said front and back fabric substructures and intervening needle loops formed in a common wale of successive courses of the other of said front and back fabric substructures.

2. A warp knitted textile spacer fabric according to claim 1, wherein said monofilament pile yarns are of relatively fine deniers in the range of about 40 denier and less.

3. A warp knitted textile spacer fabric according to claim 2, wherein said monofilament pile yarns are of relatively fine deniers in the range of about 30 denier and less.

4. A warp knitted textile spacer fabric according to claim 2, wherein said monofilament pile yarns are polyester.

5. A warp knitted textile spacer fabric according to claim 1, wherein said stretchable yarns are elastic yarns.

6. A warp knitted textile spacer fabric according to claim 1, wherein said ground yarns are dyeable by a heat transfer dye process.

7. A warp knitted textile spacer fabric according to claim 1, wherein each pile yarn of said two sets of pile yarns is formed in successive needle loops which alternate every course between non-corresponding wales of said front and back fabric substructures.

8. A warp knitted textile spacer fabric according to claim 7, wherein the successive needle loops of each pile yarn of said two sets of pile yarns comprise alternating needle loops formed alternatingly in spaced wales of successive courses of one of said front and back fabric substructures and intervening needle loops formed in a common wale of successive courses of the other of said front and back fabric substructures.

9. A warp knitted textile spacer fabric according to claim 8, wherein said spaced wales of said alternating pile yarn needle loops are separated by at least one intervening wale of said one fabric substructure.

10. A warp knitted textile spacer fabric according to claim 9, wherein one said set of monofilament pile yarns are warp knitted between said front and back fabric substructures in a 1-0, 2-3, 4-5, 3-2 stitch construction and the other said set of monofilament pile yarns are warp knitted between said front and back fabric substructures in a 5-4, 2-3, 0-1, 3-2 stitch construction.

11. A warp knitted textile spacer fabric according to claim 9, wherein one said set of monofilament pile yarns are warp knitted between said front and back fabric substructures in a 1-0, 1-2, 2-3, 2-1 stitch construction and the other said set of monofilament pile yarns are warp knitted between said front and back fabric substructures in a 2-3, 2-1, 1-0, 1-2 stitch construction.

12. A warp knitted textile spacer fabric according to claim 9, wherein one said set of monofilament pile yarns are warp knitted between said front and back fabric substructures in a 1-0, 2-3, 4-5, 3-2 stitch construction and the other said set of monofilament pile yarns are warp knitted between said front and back fabric substructures in a 4-5, 3-2, 1-0, 2-3 stitch construction.

13. A warp knitted textile spacer fabric according to claim 9, wherein one said set of monofilament pile yarns are warp knitted between said front and back fabric substructures in a 1-0, 3-4, 6-7, 4-3 stitch construction and the other said set of monofilament pile yarns are warp knitted between said front and back fabric substructures in a 6-7, 4-3, 1-0, 3-4 stitch construction.

14. A warp knitted textile spacer fabric according to claim 9, wherein one said set of monofilament pile yarns are warp knitted between said front and back fabric substructures in a 1-0, 4-5, 8-9, 5-4 stitch construction and the other said set of monofilament pile yarns are warp knitted between said front and back fabric substructures in an 8-9, 5-4, 1-0, 4-5 stitch construction.

15. A warp knitted textile spacer fabric according to claim 8, wherein said spaced wales of said alternating pile yarn needle loops are separated by at least three intervening wales of said one fabric substructure.

16. A warp knitted textile spacer fabric according to claim 8, wherein said spaced wales of said alternating pile yarn needle loops are separated by at least five intervening wales of said one fabric substructure.

17. A warp knitted textile spacer fabric according to claim 8, wherein said spaced wales of said alternating pile yarn needle loops are separated by at least seven intervening wales of said one fabric substructure.

18. A warp knitted textile spacer fabric according to claim 1, wherein each said ground yarn of one of said front and back fabric substructures is warp knitted in an 0-1, 1-1, 3-2, 2-2 stitch construction, each said stretchable yarn of said one fabric substructure is warp knitted in a 2-1, 1-1, 0-1, 1-1 stitch construction, each said ground yarn of the other fabric substructure is warp knitted in a 1-1, 3-2, 2-2, 0-1 stitch construction, and each said stretchable yarn of said other fabric substructure is warp knitted in a 1-1, 0-1, 1-1, 2-1 stitch construction.

19. A warp knitted textile spacer fabric according to claim 1, wherein said pile segments of said two sets of pile yarns cooperate to act as a pyramidal system of triangularly related trusses for supporting and maintaining said front and back fabric substructures in compressible spaced parallel relation and for resisting relative shear movement thereof in response to forces exerted in directions generally parallel to said fabric substructures.

20. An athletic shoe comprising a cushioning component formed of said textile fabric of claim 1.

21. An athletic shoe according to claim 20, wherein said cushioning component is a sleeve-like bootie integrally formed interiorly within the shoe for receiving a wearer's foot.

22. An athletic shoe according to claim 20, wherein said cushioning component is an insole.

23. An athletic shoe according to claim 20, wherein said cushioning component is a tongue.

24. A limb support device comprising said textile fabric of claim 1.

25. A limb support device according to claim 24 and further comprising a wrap for a human joint wherein said wrap is formed of said textile fabric.

26. A warp knitted textile spacer fabric of the double needle bar Raschel pile type having characteristics of stretchability, compressibility and resiliency simulative of resilient plastic foam materials and having characteristics of air and moisture permeability substantially enhanced over said foam materials, said spacer fabric comprising front and back stretchable fabric substructures and a pile substructure integrated with and extending between the front and back fabric substructures for maintaining the front and back fabric substructures in spaced parallel relation and being resiliently yieldable for compressibility of the front and back fabric substructures together and subsequent recovery thereof to spaced parallel relation, said spacer fabric being of an at least seven-bar ward knitted Raschel construction wherein each said fabric substructure comprises at least a set of ground yarns and a set of stretchable yarns interknitted with one another in a stretchable resilient stitch construction and said pile substructure comprises at least two sets of monofilament pile yarns interknitted with each said fabric substructure in a stitch construction forming pile segments which extend transversely between said fabric substructures in differing angular orientations relative thereto for permitting resilient compressibility of said fabric substructures while resisting relative shear movement of said fabric substructures in directions parallel thereto and a third set of monofilament pile yarns interknitted with each said fabric substructure in a chain stitch construction forming pile segments which extend transversely between said fabric substructures.

27. A warp knitted textile spacer fabric according to claim 26, wherein each pile yarn of said third set of pile yarns is formed in successive needle loops which alternate every course between corresponding wales of said front and back fabric substructures.

28. A warp knitted textile spacer fabric according to claim 27, wherein said third set of monofilament pile yarns are warp knitted between said front and back fabric substructures in a 1-0, 0-1, 0-1, 1-0 chain stitch construction.

29. A warp knitted textile spacer fabric according to claim 27, wherein said third set of monofilament pile yarns are warp knitted between said front and back fabric substructures in a 1-0, 0-0, 0-0, 0-1, 1-1, 1-1 chain stitch construction.

30. A warp knitted textile spacer fabric according to claim 27, wherein said pile segments of said three sets of pile yarns cooperate to act as a pyramidal system of triangularly related trusses for supporting and maintaining said front and back fabric substructures in compressible spaced parallel relation and for resisting relative shear movement thereof in response to forces exerted in directions generally parallel to said fabric substructures.

31. An athletic shoe comprising a cushioning component formed of said textile fabric of claim 30.

32. A limb support device comprising said textile fabric of claim 30.

33. A warp knitted textile spacer fabric according to claim 30, wherein each said triangularly related truss comprises six pile segments including a pair of pile segments of each of said three sets of pile yarns, said six pile segments extending from six respective spaced-apart needle loops formed in one of said front and back fabric substructures and converging together in six respective plated needle loops of said pile yarns formed in a common course and wale of the other of said front and back fabric substructures.

34. A warp knitted textile spacer fabric according to claim 33, wherein each said ground yarn of one of said front and back fabric substructures is warp knitted in an 0-1, 1-1, 3-2, 2-2 stitch construction, each said stretchable yarn of said one fabric substructure is warp knitted in a 2-1, 1-1, 0-1, 1-1 stitch construction, each said ground yarn of the other fabric substructure is warp knitted in a 1-1, 3-2, 2-2, 0-1 stitch construction, and each said stretchable yarn of said other fabric substructure is warp knitted in a 1-1, 0-1, 1-1, 2-1 stitch construction.

35. An athletic shoe comprising a cushioning component formed of said textile fabric of claim 33.

36. A limb support device comprising said textile fabric of claim 33.

37. A warp knitted textile spacer fabric according to claim 26, wherein each said ground yarn of one of said front and back fabric substructures is warp knitted in an 0-1, 1-1, 3-2, 2-2 stitch construction, each said stretchable yarn of said one fabric substructure is warp knitted in a 2-1, 1-1, 0-1, 1-1 stitch construction, each said ground yarn of the other fabric substructure is warp knitted in a 1-1, 3-2, 2-2, 0-1 stitch construction, and each said stretchable yarn of said other fabric substructure is warp knitted in a 1-1, 0-1, 1-1, 2-1 stitch construction.

38. An athletic shoe comprising a cushioning component formed of said textile fabric of claim 26.

39. A limb support device comprising said textile fabric of claim 26.

40. A warp knitted textile spacer fabric of the double needle bar Raschel pile type having characteristics of stretchability, compressibility and resiliency simulative of resilient plastic foam materials and having characteristics of air and moisture permeability substantially enhanced over said foam materials, said spacer fabric comprising front and back stretchable fabric substructures and a pile substructure integrated with and extending between the front and back fabric substructures for maintaining the front and back fabric substructures in spaced parallel relation and being resiliently yieldable for compressibility of the front and back fabric substructures together and subsequent recovery thereof to spaced parallel relation, said spacer fabric being of an at least six-bar warp knitted Raschel construction wherein each said fabric substructure comprises at least a set of ground yarns and a set of stretchable yarns interknitted with one another in a stretchable resilient stitch construction having needle loops of said ground and stretchable yarns arranged in longitudinal wales and transverse courses and said pile substructure comprises at least two sets of monofilament pile yarns interknitted with each said fabric substructure in a stitch construction forming pile segments which extend transversely between said fabric substructures in differing angular orientations relative thereto for permitting resilient compressibility of said fabric substructures while resisting relative shear movement of said fabric substructures in directions parallel thereto, said pile segments of said two sets of pile yarns cooperating to act as a pyramidal system of triangularly related trusses for supporting and maintaining said front and back fabric substructures in compressible spaced parallel relation and for resisting relative shear movement thereof in response to forces exerted in directions generally parallel to said fabric substructures, each said triangularly related truss comprising four pile segments including a pair of pile segments of each of said two sets of pile yarns, said four pile segments extending from four respective spaced-apart needle loops formed in one of said front and back fabric substructures and converging together in four respective plated needle loops of said pile yarns formed in a common course and wale of the other of said front and back fabric substructures.

41. An athletic shoe comprising a cushioning component formed of said textile fabric of claim 40.

42. A limb support device comprising said textile fabric of claim 40.

43. A process for producing a warp knitted spacer fabric of the double needle bar Raschel pile type having characteristics of stretchability, compressibility and resiliency simulative of resilient plastic foam materials and having characteristics of air and moisture permeability substantially enhanced over said foam materials, said process comprising the steps of warp knitting on a double needle bar Raschel knitting machine having at least six yarn guide bars an at least six bar spacer fabric comprising front and back stretchable fabric substructures and a pile substructure integrated with and extending between the front and back fabric substructures for maintaining the front and back fabric substructures in spaced parallel relation and being resiliently yieldable for compressibility of the front and back fabric substructures together and subsequent recovery thereof to spaced parallel relation, said knitting steps comprising forming each said fabric substructure by interknitting at least a set of ground yarns and a set of stretchable yarns with one another in a stretchable resilient stitch construction having needle loops of said ground and stretchable yarns arranged in longitudinal wales and transverse courses and forming said pile substructure by interknitting at least two sets of monofilament pile yarns with each said fabric substructure in a stitch construction forming pile segments which extend transversely between said fabric substructures in differing angular orientations relative thereto for permitting resilient compressibility of said fabric substructures while resisting relative shear movement of said fabric substructures in directions parallel thereto and forming each pile yarn of at least one of said two sets of pile yarns in successive needle loops which alternate every course between non-corresponding wales of said front and back fabric substructures including alternating needle loops arranged alternatingly in spaced wales of successive courses of one of said front and back fabric substructures and intervening needle loops arranged in a common wale of successive courses of the other of said front and back fabric substructures.

44. A process for producing a warp knitted spacer fabric according to claim 43 and further comprising the steps of, after knitting, stretching said spacer fabric into a predetermined stretched condition wherein said spacer fabric retains a desired degree of residual stretchability, compressibility and resiliency while said monofilament pile yarns are substantially withdrawn interiorly into said spacer fabric from said fabric substructures and, while maintaining said spacer fabric in said stretched condition, heat setting said spacer fabric to fix said spacer fabric dimensionally and structurally in said stretched condition.

45. A process for producing a warp knitted spacer fabric according to claim 43 and further comprising heat transfer printing of at least one of said fabric substructures.

46. A process for producing a warp knitted textile spacer fabric according to claim 43, wherein said warp knitting step comprises forming each of said front and back substructures in needle loops of said ground and stretchable yarns arranged in longitudinal wales and transverse courses and forming each pile yarn of said two sets of pile yarns in successive needle loops which alternate every course between non-corresponding wales of said front and back fabric substructures.

47. A process for producing a warp knitted textile spacer fabric according to claim 46, wherein said warp knitting step comprises forming the successive needle loops of each pile yarn of said two sets of pile yarns in alternating needle loops arranged alternatingly in spaced wales of successive courses of one of said front and back fabric substructures and intervening needle loops arranged in a common wale of successive courses of the other of said front and back fabric substructures.

48. A process for producing a warp knitted textile spacer fabric according to claim 47, wherein said spaced wales of said alternating pile yarn needle loops are separated by at least one intervening wale of said one fabric substructure.

49. A process for producing a warp knitted textile spacer fabric according to claim 48, wherein said warp knitting step comprises knitting one said set of monofilament pile yarns between said front and back fabric substructures in a 1-0, 2-3, 4-5, 3-2 stitch construction and knitting the other said set of monofilament pile yarns between said front and back fabric substructures in a 5-4, 2-3, 0-1, 3-2 stitch construction.

50. A warp knitted textile spacer fabric according to claim 48, wherein said warp knitting step comprises knitting one said set of monofilament pile yarns between said front and back fabric substructures in a 1-0, 1-2, 2-3, 2-1 stitch construction and knitting the other said set of monofilament pile yarns between said front and back fabric substructures in a 2-3, 2-1, 1-0, 1-2 stitch construction.

51. A process for producing a warp knitted textile spacer fabric according to claim 48, wherein said warp knitting step comprises knitting one said set of monofilament pile yarns between said front and back fabric substructures in a 1-0, 2-3, 4-5, 3-2 stitch construction and knitting the other said set of monofilament pile yarns between said front and back fabric substructures in a 4-5, 3-2, 1-0, 2-3 stitch construction.

52. A process for producing a warp knitted textile spacer fabric according to claim 48, wherein one said set of monofilament pile yarns are warp knitted between said front and back fabric substructures in a 1-0, 3-4, 6-7, 4-3 stitch construction and the other said set of monofilament pile yarns are knitted between said front and back fabric substructures in a 6-7, 4-3, 1-0, 3-4 stitch construction.

53. A process for producing a warp knitted textile spacer fabric according to claim 48, wherein one said set of monofilament pile yarns are warp knitted between said front and back fabric substructures in a 1-0, 4-5, 8-9, 5-4 stitch construction and the other said set of monofilament pile yarns are knitted between said front and back fabric substructures in an 8-9, 5-4, 1-0, 4-5 stitch construction.

54. A process for producing a warp knitted textile spacer fabric according to claim 47, wherein said spaced wales of said alternating pile yarn needle loops are separated by at least three intervening wales of said one fabric substructure.

55. A process for producing a warp knitted textile spacer fabric according to claim 47, wherein said spaced wales of said alternating pile yarn needle loops are separated by at least five intervening wales of said one fabric substructure.

56. A process for producing a warp knitted textile spacer fabric according to claim 47, wherein said spaced wales of said alternating pile yarn needle loops are separated by at least seven intervening wales of said one fabric substructure.

57. A process for producing a warp knitted textile spacer fabric according to claim 43, wherein said warp knitting step comprises forming said pile segments of said two sets of pile yarns to act cooperatively as a pyramidal system of triangularly related trusses for supporting and maintaining said front and back fabric substructures in compressible spaced parallel relation and for resisting relative shear movement thereof in response to forces exerted in directions generally parallel to said fabric substructures.

58. A process for producing a warp knitted spacer fabric according to claim 43 and further comprising the step of, prior to said warp knitting step, preparing a respective warp beam of each said set of ground, stretchable and pile yarns and heat transfer printing of at least one set of said ground yarns while in warp sheet form.

59. A process for producing a warp knitted textile spacer fabric according to claim 43, wherein said warp knitting step comprises knitting each said ground yarn of one of said front and back fabric substructures in a 0-1, 1-1, 3-2, 2-2 stitch construction, knitting each said stretchable yarn of said one fabric substructure in a 2-1, 1-1, 0-1, 1-1 stitch construction, knitting each said body yarn of the other fabric substructure in a 1-1, 3 -2, 2 -2, 0-1 stitch construction, and knitting each said stretchable yarn of said other fabric substructure in a 1-0, 0-1, 1-1, 2-1 stitch construction.

60. A process for producing a warp knitted spacer fabric of the double needle bar Raschel pile type having characteristics of stretchability, compressibility and resiliency simulative of resilient plastic foam materials and having characteristics of air and moisture permeability substantially enhanced over said foam materials, said process comprising the steps of warp knitting on a double needle bar Raschel knitting machine having at least seven yarn guide bars an at least seven bar spacer fabric comprising front and back stretchable fabric substructures and a pile substructure integrated with an extending between the front and back fabric substructures for maintaining the front and back fabric substructures in spaced parallel relation and being resiliently yieldable for compressibility of the front and back fabric substructures together and subsequent recovery thereof to spaced parallel relation, said knitting steps comprising forming each said fabric substructure by interknitting at least a set of ground yarns and a set of stretchable yarns with one another in a stretchable resilient stitch construction and forming said pile substructure by interknitting at least two sets of monofilament pile yarns with each said fabric substructure in a stitch construction forming pile segments which extend transversely between said fabric substructures in differing angular orientations relative thereto for permitting resilient compressibility of said fabric substructures while resisting relative shear movement of said fabric substructures in directions parallel thereto and knitting a third set of monofilament pile yarns with each said fabric substructure in a chain stitch construction forming pile segments which extend transversely between said fabric substructures.

61. A process for producing a warp knitted textile spacer fabric according to claim 60, wherein said warp knitting step comprises forming each pile yarn of said third set of pile yarns in successive needle loops which alternate every course between corresponding wales of said front and back fabric substructures.

62. A process for producing a warp knitted textile spacer fabric according to claim 61, wherein said warp knitting step comprises knitting said third set of monofilament pile yarns between said front and back fabric substructures in a 1-0, 0-1, 0-1, 1-0 chain stitch construction.

63. A process for producing a warp knitted textile spacer fabric according to claim 61, wherein said warp knitting step comprises knitting said third set of monofilament pile yarns between said front and back fabric substructures in a 1-0, 0-0, 0-0, 0-1, 1-1, 1-1 chain stitch construction.

64. A process for producing a warp knitted textile spacer fabric according to claim 61, wherein said warp knitting step comprises forming said pile segments of said three sets of pile yarns to act cooperatively as a pyramidal system of triangularly related trusses for supporting and maintaining said front and back fabric substructures in compressible spaced parallel relation and for resisting relative shear movement thereof in response to forces exerted in directions generally parallel to said fabric substructures.

65. A process for producing a warp knitted textile spacer fabric according to claim 64, wherein said warp knitting step comprises forming each said triangularly related truss to comprise six pile segments including a pair of pile segments of each of said three sets of pile yarns, said six pile segments extending from six respective spaced-apart needle loops formed in one of said front and back fabric substructures and converging together in six respective plated needle loops of said pile yarns formed in a common course and wale of the other of said front and back fabric substructures.

66. A process for producing a warp knitted textile spacer fabric according to claim 65, wherein said warp knitting step comprises knitting each said ground yarn of one of said front and back fabric substructures in a 0-1, 1-1, 3-2, 2-2 stitch construction, knitting each said stretchable yarn of said one fabric substructure in a 2-1, 1-1, 0-1, 1-1 stitch construction, knitting each said body yarn of the other fabric substructure in a 1-1, 3-2, 2-2, 0-1 stitch construction, and knitting each said stretchable yarn of said other fabric substructure in a 1-1, 0-1, 1-1, 2-1 stitch construction.

67. A process for producing a warp knitted textile spacer fabric according to claim 60, wherein said warp knitting step comprises knitting each said ground yarn of one of said front and back fabric substructures in a 0-1, 1-1, 3-2, 2-2 stitch construction, knitting each said stretchable yarn of said one fabric substructure in a 2-1, 1-1, 0-1, 1-1 stitch construction, knitting each said body yarn of the other fabric substructure in a 1-1, 3-2, 2-2, 0-1 stitch construction, and knitting each said stretchable yarn of said other fabric substructure in a 1-1, 0-1, 1-1, 2-1 stitch construction.

68. A process for producing a warp knitted spacer fabric of the double needle bar Raschel pile type having characteristics of stretchability, compressibility and resiliency simulative of resilient plastic foam materials and having characteristics of air and moisture permeability substantially enhanced over said foam materials, said process comprising the steps of warp knitting on a double needle bar Raschel knitting machine having at least six yarn guide bars an at least six bar spacer fabric comprising front and back stretchable fabric substructures and a pile substructure integrated with and extending between the front and back fabric substructures for maintaining the front and back fabric substructures in spaced parallel relation and being resiliently yieldable for compressibility of the front and back fabric substructures together and subsequent recovery thereof to spaced parallel relation, said knitting steps comprising forming each said fabric substructure by interknitting at least a set of ground yarns and a set of stretchable yarns with one another in a stretchable resilient stitch construction having needle loops of said ground and stretchable yarns arranged in longitudinal wales and transverse courses and forming said pile substructure by interknitting at least two sets of monofilament pile yarns with each said fabric substructure in a stitch construction forming pile segments which extend transversely between said fabric substructures in differing angular orientations relative thereto for permitting resilient compressibility of said fabric substructures while resisting relative shear movement of said fabric substructures in directions parallel thereto, said interknitting said pile yarns comprising forming said pile segments of said two sets of pile yarns to act cooperatively as a pyramidal system of triangularly related trusses for supporting and maintaining said front and back fabric substructures in compressible spaced parallel relation and for resisting relative shear movement thereof in response to forces exerted in directions generally parallel to said fabric substructures by forming each said triangularly related truss to comprise four pile segments including a pair of pile segments of each of said two sets of pile yarns, said four pile segments extending from four respective spaced-apart needle loops formed in one of said front and back fabric substructures and converging together in four respective plated needle loops of said pile yarns formed in a common course and wale of the other of said front and back fabric substructures.

* * * * *